(12) United States Patent
Pan et al.

(10) Patent No.: US 10,481,021 B2
(45) Date of Patent: Nov. 19, 2019

(54) SUPERCAPACITIVE IONTRONIC NANOFABRIC SENSING ASSEMBLIES

(71) Applicants: TACSENSE, INC., Woodland, CA (US); THE REGENTS OF THE UNIVERSITY OF CALIFORNIA, Oakland, CA (US)

(72) Inventors: Tingrui Pan, Woodland, CA (US); Ruya Li, Beijing (CN); Benjamin Arthur Bazor, Davis, CA (US)

(73) Assignee: TACSENSE, INC., Woodland, CA (US)

( * ) Notice: Subject to any disclaimer, the term of this patent is extended or adjusted under 35 U.S.C. 154(b) by 0 days.

(21) Appl. No.: 15/990,564

(22) Filed: May 25, 2018

(65) Prior Publication Data

US 2018/0340847 A1 Nov. 29, 2018

Related U.S. Application Data

(60) Provisional application No. 62/511,330, filed on May 25, 2017.

(51) Int. Cl.
*G01L 1/00* (2006.01)
*G01L 1/14* (2006.01)
(Continued)

(52) U.S. Cl.
CPC .............. *G01L 1/146* (2013.01); *A41D 1/002* (2013.01); *A41D 13/1281* (2013.01); *A41D 19/0027* (2013.01); *A41D 25/00* (2013.01); *A41D 27/205* (2013.01); *A61B 5/447* (2013.01); *A61B 5/6803* (2013.01); *A61B 5/6804* (2013.01);
(Continued)

(58) Field of Classification Search
CPC ..... G01L 1/146; A41D 1/002; A41D 13/1281; A41D 19/0027; A41D 25/00; A41D 27/205; A43B 3/0005; A61B 5/447; A61B 5/6803; A61B 5/6806; A61B 2503/10; A61B 2505/05; A61B 2562/0247; A61B 2562/0285; B32B 5/022; B32B 5/024; B32B 2307/202; B32B 2437/02;
(Continued)

(56) References Cited

U.S. PATENT DOCUMENTS

2002/0197622 A1* 12/2002 McDevitt ......... G01N 33/54366
435/6.12
2008/0195018 A1* 8/2008 Larson ............... A61B 17/1325
602/53

(Continued)

*Primary Examiner* — Max H Noori
(74) *Attorney, Agent, or Firm* — Kurt T. Mulville; VLP Law Group, LLP

(57) ABSTRACT

A fabric-based pressure sensor assembly utilizing in ionic material and conductive material is disclosed. The sensing device can be applied in several various wearable health and biomedical applications on complex body topologies. As an alternative to conventional flexible sensors, the fabric-based sensor assembly yields high device sensitivity and desirable parameters for pressure sensing in a wearable construct. The sensor assembly enables rapid mechanical responses (in the milliseconds range) for high-frequency biomechanical signals, e.g., blood pressure pulses and body movements. The fabrication process for the device is low-cost highly compatible with existing industrial manufacturing processes.

12 Claims, 13 Drawing Sheets

(51) Int. Cl.
| | |
|---|---|
| *D03D 15/00* | (2006.01) |
| *B32B 5/02* | (2006.01) |
| *A41D 25/00* | (2006.01) |
| *A41D 1/00* | (2018.01) |
| *A41D 19/00* | (2006.01) |
| *A41D 27/20* | (2006.01) |
| *A61B 5/00* | (2006.01) |
| *D03D 1/00* | (2006.01) |
| *A41D 13/12* | (2006.01) |
| *A43B 3/00* | (2006.01) |
| *A43B 7/14* | (2006.01) |
| *A43B 13/02* | (2006.01) |
| *A43B 23/02* | (2006.01) |

(52) U.S. Cl.
CPC ............ *A61B 5/6806* (2013.01); *B32B 5/022* (2013.01); *B32B 5/024* (2013.01); *D03D 1/0088* (2013.01); *D03D 15/00* (2013.01); *A43B 3/0005* (2013.01); *A43B 7/147* (2013.01); *A43B 13/02* (2013.01); *A43B 23/0205* (2013.01); *A61B 2503/10* (2013.01); *A61B 2505/05* (2013.01); *A61B 2562/0247* (2013.01); *A61B 2562/0285* (2013.01); *B32B 2307/202* (2013.01); *B32B 2437/02* (2013.01); *D10B 2401/16* (2013.01); *D10B 2501/041* (2013.01); *D10B 2501/043* (2013.01)

(58) Field of Classification Search
CPC .. D03D 1/0088; D03D 15/00; D10B 2401/16; D10B 2501/041; D10B 2501/043
USPC .................................................... 73/862.046
See application file for complete search history.

(56) References Cited

U.S. PATENT DOCUMENTS

| | | | |
|---|---|---|---|
| 2010/0141085 A1* | 6/2010 | Wu | C08J 5/2256 310/311 |
| 2012/0128995 A1* | 5/2012 | Leto | C09D 175/04 428/473 |
| 2015/0354131 A1* | 12/2015 | Haq | B32B 5/26 428/208 |
| 2016/0058092 A1* | 3/2016 | Aldino | A42B 3/046 2/412 |
| 2017/0059434 A1* | 3/2017 | Li | G01L 9/0072 |
| 2017/0136180 A1* | 5/2017 | Zhao | A61K 9/0009 |

* cited by examiner

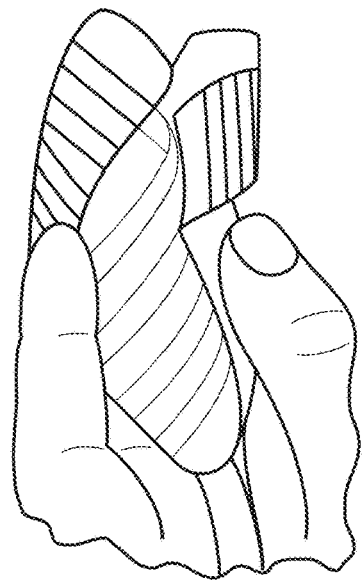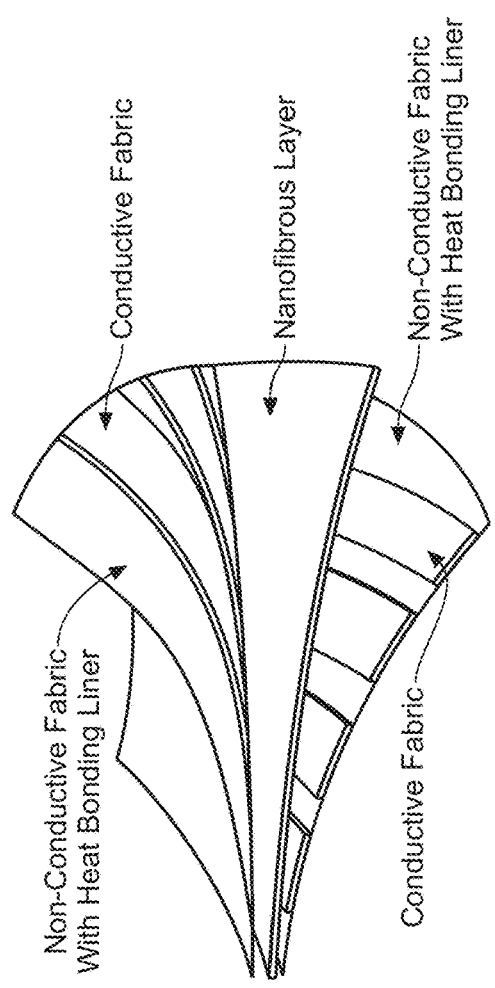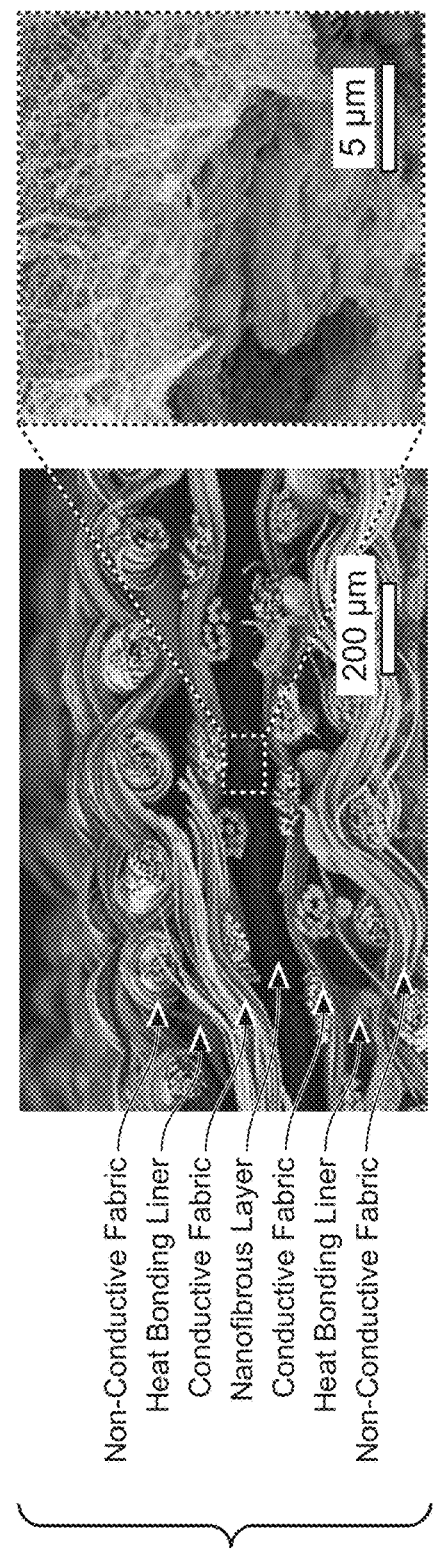
FIG. 1A
FIG. 1B
FIG. 1C

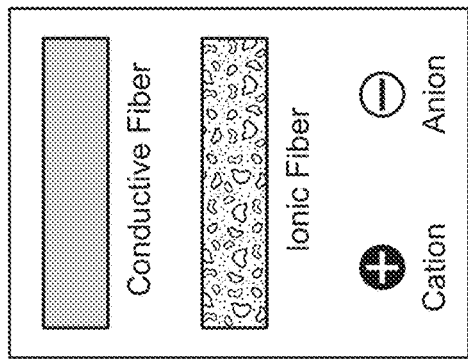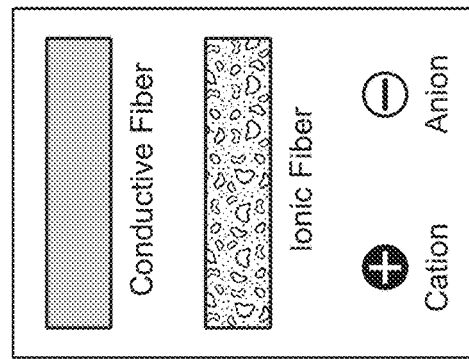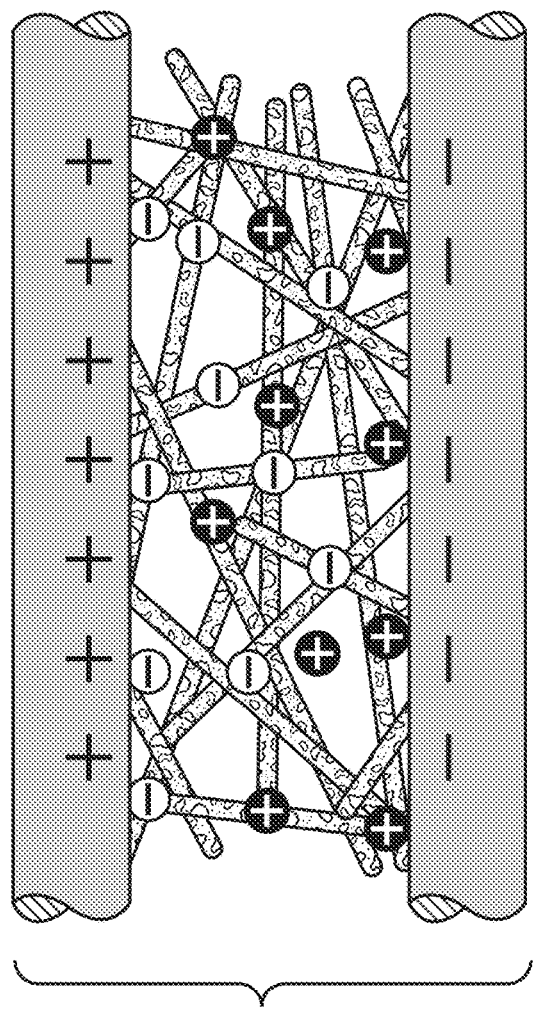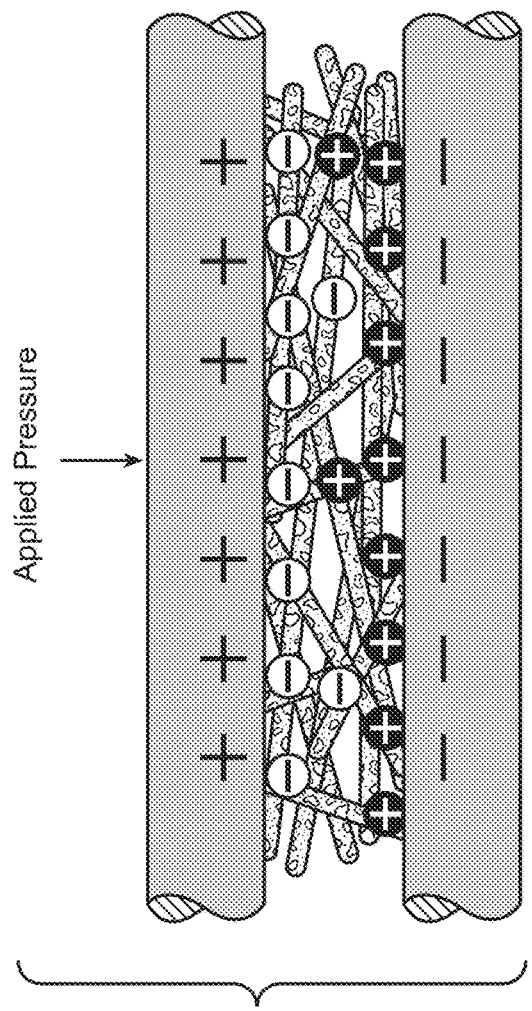
FIG. 1D
FIG. 1E

P(VDF-HFP)

[EMIM][TFSI]

P(VDF-HFP)

[EMIM][TFSI]

P(VDF-HFP)

[EMIM][TFSI]

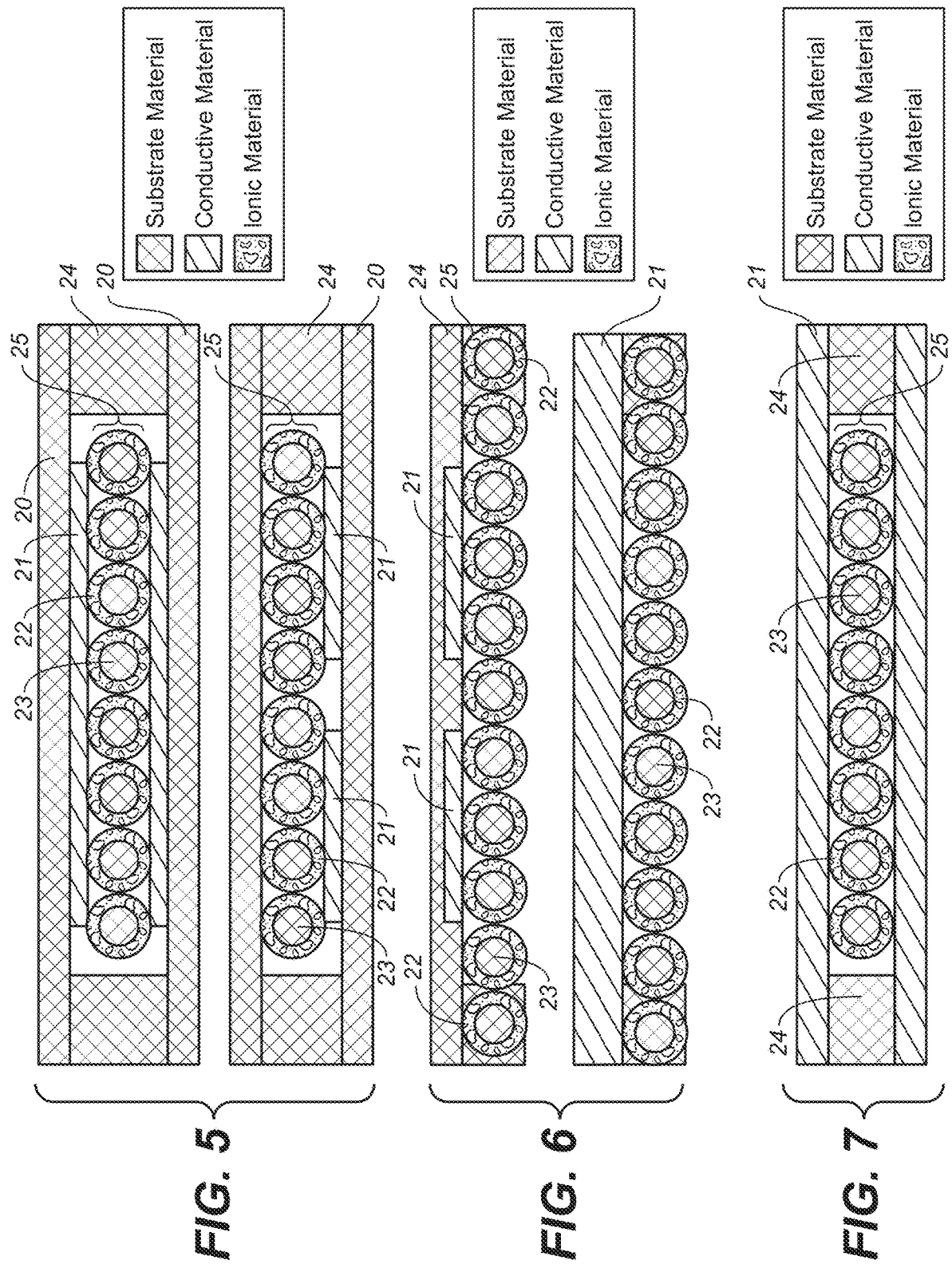

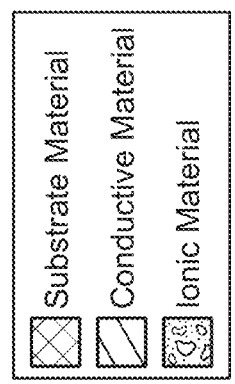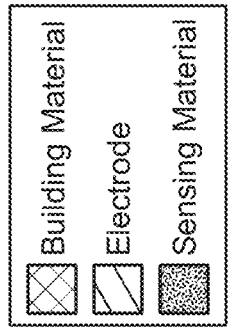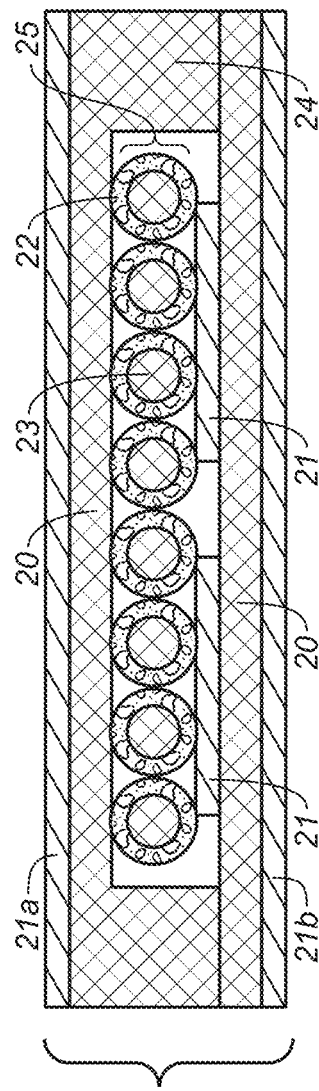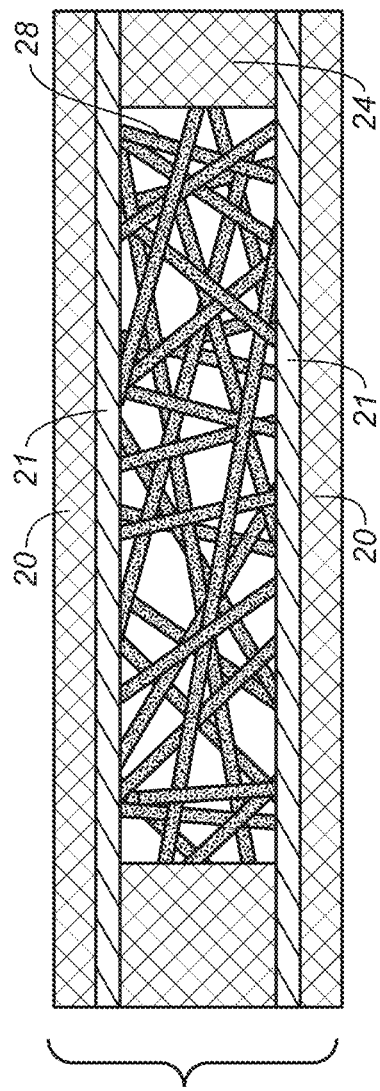
FIG. 9
FIG. 10

SUPERCAPACITIVE IONTRONIC NANOFABRIC SENSING ASSEMBLIES

CROSS REFERENCE TO RELATED APPLICATIONS

The present application claims priority to U.S. provisional application entitled "SUPER-CAPACITIVE IONTRONIC NANOFABRIC SENSING," Application No. 62/511,330, filed May 25, 2017. The Provisional Application is hereby incorporated by reference in its entirety.

REFERENCE TO GOVERNMENT

This invention was made with Government support under NSF Awards Nos. ECCS-1307831. The Government has certain rights in this invention.

BACKGROUND OF THE INVENTION

Sensors that detect and monitor human surroundings and communicate acquired physical data, such as pressure, shear, strain, and other physical inputs, enable the creation of a number of useful devices having application from consumer electronics to healthcare and biomedical monitoring. The increasing demand to measure and store a wide range of sensor data places significant demand on the design and development of new sensor technologies. Moreover, the need to incorporate these sensors into wearable articles that are in intimate contact with the body requires that the sensors and their related assemblies be lightweight, flexible, an offer extremely favorable performance parameters including long-term stability, high sensitivity, low profile dimensions, low signal-to-noise ratio, and extremely rapid response rates. Where the sensors are incorporated into a wearable item, the structures must be suitable for integration with fibrous or cloth substrates, such as fabrics ordinarily used for garments. Fabrics offer an attractive platform for wearable sensors because fabrics have high degrees of deformability, conformability, long-term stability, can place high performance sensors in intimate contact with the body potentially without compromising either the wearability of the fabric substrate or the performance of the sensor.

The design of the such sensors must take into account the structural characteristics of the fabric material in which the sensor will be located. A sensor that it is in flexible or cannot withstand repetitive motion would not be usable in combination with fabric used in article of clothing that is expected to be repeatedly exposed to variable pressures and sheer forces generated during ordinary wear. Similarly, a sensor that is inoperative, or which loses sensing capacity, in the presence of moisture would not be an effective sensor for many article of clothing that are expected to get wet in ordinary usage. Accordingly, an ideal sensor must balance competing needs: 1) the sensor must satisfy a number of technical sensing parameters to generate high quality data, such as small changes in pressure, to make the sensor useful for a wide variety of purposes, and 2) the sensor assembly must be able to be integrated with the fabric material while remaining the capability to collect high-quality sensor data under all of the external conditions imposed on the fabric material, including for example repetitive motion, stretching, bending, and twisting forces as might be expected for ordinary fabric.

Moreover, flexible and wearable sensors must provide accurate and reliable sensing data without compromising the natural movement and comfort of the user, otherwise the data would not be useful and utility of the sensor in ordinary wearable applications would be greatly diminished. An additional challenge is the ability of the sensor to be incorporated in a flexible, wearable substrate during manufacture of the combination of the fabric and the sensor such that neither the sensing function nor the fabric quality is compromised during manufacture and that the resulting article remains capable of high quality data collection and transmission.

Fabric offers an ideal platform for wearable sensors to detect physiological and health data. Because of the intimate contact with the skin, sensors can be incorporated directly into wearable clothing fabric with little impact on the normal activities of the user. A fabric-based sensor works best when it is held close to the skin. To achieve close conformity to the skin, a wide variety of polymer materials have been used due to ease of manufacture and inherent flexibility. As long as the technical capabilities of the sensing element are compatible with the task of data collection in a fabric platform and subsequent transmission to a data processing unit, a variety of clothing items can be modified to contain sensors to detect data. Depending on the construction of the fabric article, such as a piece of clothing, and the particular the physiological data that is to be collected, the integration of pressure sensors into the fabric may have little or no impact on wearability.

Existing pressure sensors tend to be based on three classic sensing mechanisms: 1) a flexible conductor mode, 2) a piezoelectric-based detection mode, and 3) a parallel-plate capacitance configuration. Currently, the flexible resistor approach has been the primary modality for wearable applications but is plagued by slow mechanical response times and low signal-to-noise ratios that limit the signal bandwidth and resolution. Furthermore, many materials are only available for dynamic force measurement, measurable changes in pressure over time, and are not suitable for static readout, measuring pressure without necessary movement that causes pressure differential changes. The sensor wearable flexible platform combination must also account for electrical properties of the body itself that tend to limits the ability of parallel-plate capacitance based sensors to make fine pressure measurements.

Accordingly, flexible and wearable physical sensing platforms must satisfy a number of challenging, and often conflicting, design and performance parameters to permit real-time, static and dynamic, high signal/low noise, and overall high-performance data detection and processing to facilitate the practical application of new high-tech sensors to electronic, healthcare, and biomedical applications. The development of flexible and wearable sensors demands innovation in the material science of the sensor element, the fabrication process of sensor, and the creation of a sensor assembly to take advantage of the high-performance capabilities of the sensor element, while maintaining the ability to integrate the sensor assembly into a fabric-based platform.

SUMMARY OF THE INVENTION

The present invention is a high-performance, high precision sensor assembly that can be integrated into a fabric-based sensor platform for wearable electronic devices. The sensor assemblies have the ability to integrate into fibrous and non-fibrous materials, including fabric and other wearable materials. These wearable devices incorporate a specially designed fabric platform into which one or more sensor assemblies is embedded to yield extremely high sensitivity pressure measurements. The sensor assemblies feature shielding from environmental noise, optical transparency, the ability to seal the sensor assembly, extremely thin sensor layer design, and a variety of additional performance parameters that are uniquely valuable in a wearable and a fabric-based pressure sensor platform.

The adaptation of specific ionic materials as a component of the sensor enables the use of ionic materials in polymeric networks that yield a planar, multi-layered sensor assembly that has an elastic solid structure that maintains an electrical conductor in close engagement with mobile ions suspended in an ionic gel matrix. The ionic gel matrix can be integrated into the assembly by coating on a fiber, by being formed into the fibers themselves, or by being applied to the surface of a fiber are fabric substrate. The ionic material can also be disposed in a polymeric substrate for the manufacture of a sensor assembly having high elasticity, a favorable softness durometer measurement, and a low profile height dimension less than 10 μm, and as low as 1-5 μm. Because the ionic material disposed in the polymer does not require ultraviolet hearing, the assembly can be fabricated without a photo-initiator.

In some embodiments, the elastic deformation of the fabric structure exerts differential pressure on sensors comprised of mobile ions suspended within the ionic material of the applied to a fabric fabric substrate, which enables both strain and pressure-induced differential pressure measurements based on measurement of absolute or differential capacitance values. The ionic material is comprised of a threshold amount of mobile cations and anions to form a unique supercapacitive layer with high unit-area capacitance at nanometer spacing. Once in contact with an electrode, this supercapacitive layer forms an electric double layer (EDL) exhibiting desirable performance parameters in a flexible and wearable substrate.

The sensor assembly can be based on ionic material disposed in a polymer resin having a conductor disposed therein and can further integrate a fibrous or non-fibrous substrate to advantageously orient the ionic material and the conductor to detect small pressure differences as a function of changes in capacitance at the interface of the conductor and the ionic material. The sensor assembly can also be based on electrospun nanofibers, preferably in a two or three-layer sensing architecture, comprised of an electrospun nanofiber layer and a sensor layer. The polymeric layer can also be comprised of a transparent resin film that has ionic material dispersed therein or oriented to have ionic material disposed along a surface of the polymer or on a substrate that orients the ionic material and the conductor in an electrically conductive engagement such that a change in pressure alters the electrical flow through the conductor upon the application of pressure on the sensor assembly. In some embodiments, the sensor layer is disposed between two structural planar layers having ionic material and a conductor oriented therebetween. Additionally, a substrate may be interposed therein and to which the ionic material is coated, optionally along the length of fibers that form a fabric substrate.

Preferably a pair of conductive fiber substrates, that optionally include a heat activated bonding layer, is combined with the sensing element and non-conductive fabric substrates to yield an integrated wearable assembly. The combination of the layers may also be sealed about a periphery of the construct to create a moisture and liquid barrier layer. The sensor structure and materials can be varied in construction and composition to tune the sensor for prioritization of selected measurement parameters, including but not limited to horizontal and vertical elasticity, moisture and water resistance, resistance to solvents and detergents, durability from multiple, extreme or repeat stresses, flexibility and conformability in three directions, sensitivity and specificity of pressure response, grounding of signal or noise inputs, and overall noise reduction.

The desired sensing input dictates the design and selection of sensor parameters and materials used to fabricate the sensor. For example, a sensor intended to detect cardiac events, such as heart rate, pulse waveform, blood pressure, and other parameters may be designed to be affixed to pulse points such as the wrist or the carotid arteries of the neck and the sensor construct would be disposed in the fabric structural platform to facilitate collection of those types of data. Similarly, measuring muscle motion and overall body position and movement would require a different sensor array and fabric platform to detect all the necessary data and may suggest that a fundamental difference in the composition of the sensor element themselves be selected to optimize the necessary performance parameters for the particular data sought. Accordingly, the molecular structure of the iontronic matrix can be tailored to vary the composition of ionic material and the performance parameters of the sensor assembly. As disclosed below, additional selections in the structure of the sensor material, such as selection of the porosity of the components containing the ionic material, including utilization of nanofiber structure comprised of my ionic materials, patterning of the conductive materials as electrodes, and the selective placement of the ionic material, conductive material, and structural and nonstructural substrate materials allows the selective design of a sensor assembly tailors the performance parameters to the particular desired function and application of the sensor platform.

In the specific fabric-based sensor embodiments, the sensor assembly is preferably comprised of a plurality of electrodes and an iontronic fabric held in close conforming engagement such that any change in pressure alters the area of contact between the ionic material and the conductive material such that differential conductance is readily translated into a measurement of change in pressure. The electrodes may be conductive fabric, printed electrodes, or other electrode materials. The plurality of electrodes is preferably a pair of coplanar electrodes that may be patterned or unpatterned and may be sandwiched between the iontronic fabric on either side of the assembly. The iontronic fabric is a fibrous or non-fibrous paper, fiber mesh, woven fabric, paper, or other porous material that is coated with the ionic sensor material. Alternatively, the iontronic fabric may act as one of the electrodes. Because of the unique arrangement of the components of the sensor assembly, the entire assembly sensor assembly may be sealed about one or more edges of the assembly so that the entire construct is impervious to liquid.

BRIEF DESCRIPTION OF THE DRAWINGS

FIGS. 1A-1E illustrate the fabric-based pressure sensing platform comprised of a sensor assembly having a nanofiber pressure sensor showing ionic nanofibers in contact with two conductive fibers and the application of pressure in a downward vertical direction to alter the confirmation of the ionic nanofibers and conductive fibers under mechanical stimuli to yield a resulting electrical signal. Specifically, FIG. 1A is a schematic illustration of the all-fabric sensing matrix with a nanofibrous layer. FIG. 1B is a photograph of the 4×4 sensing array at a spatial resolution of 1×1 mm2. FIG. 1C are SEM photos of the device in cross-section views at 200 micrometers and 5 micrometers scale. FIGS. 1D and 1E show an operational principle of the nanofabric pressure sensor in which ionic nanofibers are in contact with two conductive fibers. Physical contacts between the ionic nanofabric and conductive fibers vary under external mechanical stimuli.

—FIG. 2A, 2B are a 2:1 ratio, FIGS. 2C, 2D are at a 1:1 ratio, FIGS. 2E and 2F are at a 1:2 ratio, respectively.

FIG. 3A contains plots of the experimental and theoretical all-fabric device sensitivity with measurement results plotted as dots and the sensitivity predicted by the theoretical model is shown with solid lines. In FIG. 3B, the device sensitivity is measured under different radii of curvature, changing from 25, 50, 100 mm to infinite (flat). In FIGS. 3C-3E, the mechanical response of an all fabric supercapacitive pressure sensing unit with an iontronic Nanofabric P(VDF-HFP):[EMIM][TFSI] 1:1 wt % is shown under varying periodic stimuli of 3C) 1 Hz, 3D) 10 Hz, and 3E) 25 Hz.

FIGS. 4A and 4B are graphic representations of a supercapacitive all-fabric facemask with a plurality e.g. 10-20 pressure sensing units disposed about the interior surface of the mask. FIG. 4B shows the orientation of the mask placed on a downward directed human face. In the application of FIG. 4B, pressure sensing facemask worn on the face is shown pressing against a foam facial pillow to exert external pressure to the facemask causing the individual sensors to engage the surface of the face. FIGS. 4C and 4D are distribution mapping resulting from application of the facemask to the human face. FIG. 4E is a glove having integrated pressure sensor assemblies in a fabric pressure-sensing construct. In FIG. 4F, an exemplary configuration of the glove showing how the pressure distribution caused by the gripping force would exert a pressure distribution on the hand. FIG. 4G shows a continuous radial arterial pulse waveform as measured noninvasively on the wrist by the fabric band shown in FIG. 4H.

FIG. 5 is embodiments of a three or more-layer structure of the sensor assembly of the invention comprised of alternate orientations of an ionic material, a conductive material, and a substrate material.

FIG. 6 is embodiments of a two or more-layer structure of the sensor and platform construct of the invention comprised of alternate orientations of an ionic material, a conductive material, and a substrate material.

FIG. 7 is an embodiment of the invention wherein the conductive material forming the electrode serves as a structural material.

FIG. 9 is an embodiment of the invention wherein the sensor element is coated with a conductive material on both sides of the assembly to reduce parasitic noises and EMF influences.

FIG. 10 is an embodiment of the invention wherein the ionic material layer is a porous material such as a woven or non-woven ionic fabric comprising the sensing material.

DETAILED DESCRIPTION OF THE INVENTION

Figure 2A:
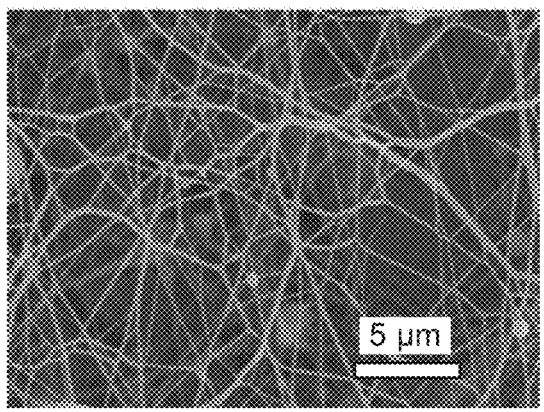
FIGS. 2A-2F are scanning electron microscope photographs (at either 5 μm or 1 μm scale as indicated) of the electrospun nanofiber structures from the ionic material comprised of P(VDF-HFP) and 1-ethyl-3-methylimidazolium bis(trifluoromethylsulfonyl) imide
Figure 2B:
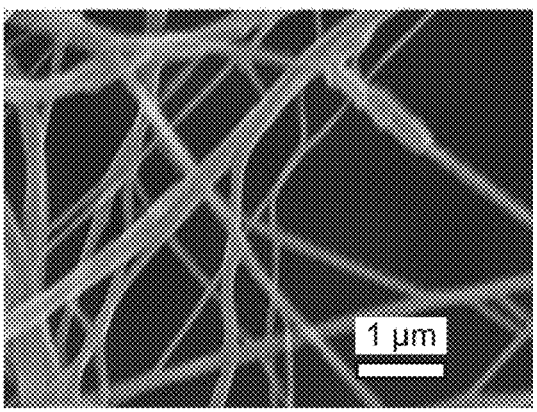
Figure 2C:
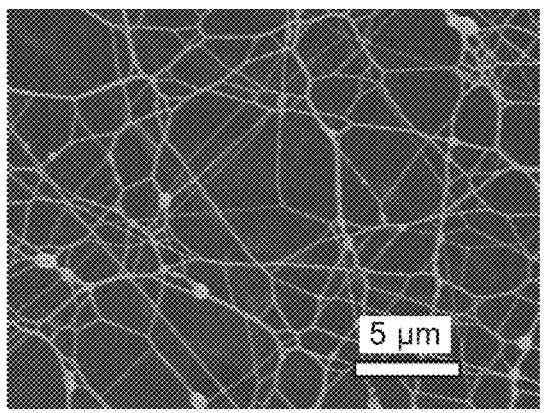
Figure 2D:
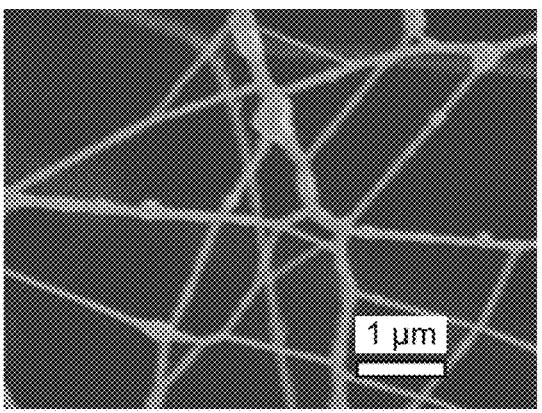
Figure 2E:
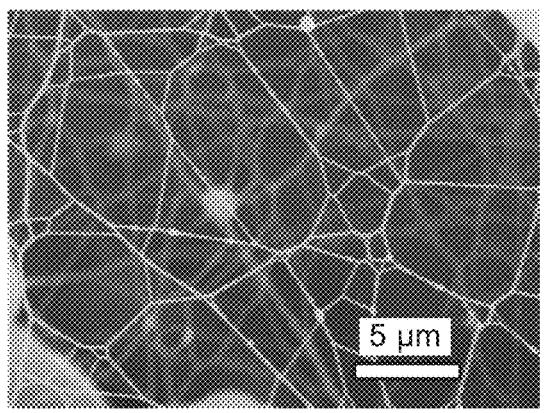
Figure 2F:
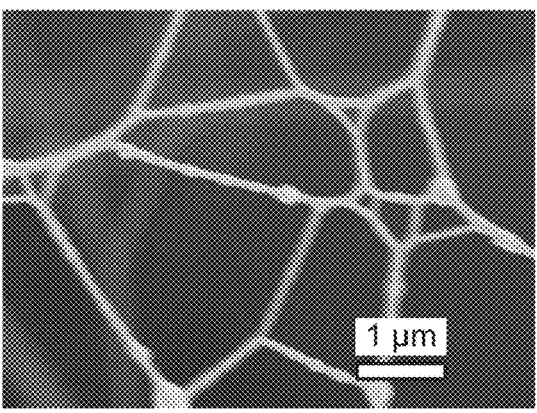

The invention comprises a supercapacitive sensor assembly, optionally integrated into a fabric based- or a film-based substrate and based on a high-performance sensor assembly using ionic sensor materials and conductive layers oriented to enable extremely sensitive pressure measurements. As described below, the sensor assembly of the invention is capable of producing a sensitivity of 114 nF kPa−1.

The sensor has a single Pascal resolution (2.4 Pa) and a millisecond mechanical response time (4.2 ms). As illustrated in the following description and Figures, under an external pressure, the contact area between ionic material in the sensor assembly and the conductive material in the sensor assembly changes with the application of pressure or a change in three-dimensional confirmation of the sensor assembly resulting in a change in electrical conductance that is correlated to extremely small changes in pressure or confirmation. In one embodiment, the ionic material is incorporated into the sensor as coating on the exterior surface of individual fibers of a fiber layer used as a component of a fabric. Portions of the exterior circumference of the fibers in contact with a conductive material change dimension in response to differential pressure or confirmation to create the differential conductance that is readable as an output signal. In such a configuration, fabric comprised of such ionic gel coated fibers would experience a structural deformation as predicted by classic a fibrous compression model and the compression and displacement of the fibers of the fabric alter the interface between the ionic material and the conductor resulting in a conductance differential related to the amount of pressure applied. The interfacial iontronic sensing capability is based on the measurement of the capacitive change of the contact area of the interface The fabric-based construction of the device maintains a high sensitivity, with only marginal variation (less than 4% sensitivity variation) under the change of surface curvature from 100 to 25 mm.

The construct of the sensor platform assembly allows detection of inertial forces caused by either or both of movement and acceleration. Pressure changes, stretch, deformation, and any exertion of force incident to the sensor assembly caused by muscle motion, static or dynamic, including deformation of any body position, yields sensory input that can be measured, collected, stored, and analyzed to produce the data output.

The arrangement of the ionic nanofiber layer and surrounding structures that make up the sensor assembly can vary as described below depending on the design of the sensor assembly and the particular performance parameters selected for the sensor assembly in combination with the remaining structures of the sensing platform device, the target body region for which the sensor or sensor array will be used, and the specific types of data desired to be collected. As shown in FIGS. 1A, 1B, 4A, 4B, 4D, and 4H, ionic pressure assembly can be layered onto or integrated into the structure of a fabric material that may be made of a plurality of layers of woven fibers. Specifically, woven conductive fibers may be layered with an ionic nanofiber structure to bring the ionic sensing material into physical contact with one or more, and preferably two conductive microfiber layers.

In the context of pressure measurement resulting from the progressive application of force to an ionic sensor assembly, an initial contact area may be defined as the area of direct contact between the ionic gel layer and a conducting layer. In one embodiment, the ionic gel layer is used to fabricate nanofibers that act as the ionic-material containing element of the sensor. Alternatively, an ionic gel or ionic matrix material may be layered onto a planar surface, disposed in a separate layer or integrated into a matrix layer with a polymer, or may be for example, coated on a substrate such as the exterior circumferential portion of a fiber. In a static state, the conductance of the sensor reflects a first position represented by a first area extent of the ionic material in electricity-conducting conformation with the conducting material. In a cloth matrix configuration, the conductance of the nanofibers is directly proportional to the area fraction of the conducting fabric in contact with the nanofiber layer.

Under the smallest external pressure, the ionic nanofiber structure experiences compression within the sensor assembly and an increased area fraction it is created at the interface of the conducting material and the ionic material. The change of the contact area is directly proportional to a variation in interfacial electrical double layer (EDL). As a result, the unit-area EDL capacitance is constant under steady state and pressure temperature and any pressure variation can be detected electronically.

In one embodiment of the sensor assembly design, a simple three-layer sensing architecture is comprised of an electrospun ionic material to fabricate a nanofibrous layer that is sandwiched between two patterned conductive fabric substrates with a heat activated bonding liner, as illustrated in FIG. 1A. The base substrates are made from commercially available textile materials. As described above under an external pressure, the contact area between the nanofibrous layer and the conductive fabric layers increases due to the structural deformation as predicted by a classic fibrous assemblies' compression model. The sensor assembly device maintains high sensitivity, with only marginal variation (less than 4% variation in the device sensitivity), under the change of surface curvatures from 100 to 25 mm. High sensitivity yields a substantial advantage in a wearable physical sensing platform even where the surface topology is highly variable, such when worn on the human body.

The operation of the sensor assembly takes advantage of a unique interfacial iontronic sensing principle resulting from the measurement of the capacitive change at the contact area of the interface. As shown in the cross-section views of the scanning electron microscopy (SEM) photos (FIG. 1C), the fibrous diameter of the conductive fabric is preferably at least two orders of magnitude greater than the diameter of the ionic layer, whereas the elastic modulus of the conductive fabric material (approximately GPa) is also orders of magnitude higher than the ionic fiber material (approximately 10 s of MPa).

The initial contact area between the ionic nanofibers and the conductive microfibers is directly proportional to the area fraction of nanofabric layer. Under external pressure, the ionic nanofibrous structure experiences an increased area fraction upon the conducting—ionic contact. The change of the contact area is directly proportional to a variation in interfacial EDL capacitance; as a result, the unit-area EDL capacitance is detected electronically and remains constant under a steady-state temperature.

The pressure-to-capacitance sensor yields a compression induced fiber area fraction with a variation that produces a corresponding capacitive change in the EDL interface. The bending of the individual fibers within the construct alters the fiber volume fraction under the compression condition. Air is extruded when the ionic nanofabric is compressed, increasing the volume fraction of the ionic fiber, that corresponding fiber area fraction increases.

For a known area with unit-area EDL capacitance of a known area with unit-area EDL capacitance of Co, the device pressure to capacitance relation can be derived as per Equation 1.

$$C = c_0 \cdot A\left(\frac{P}{\alpha \cdot E} + A_{f0}^3\right)^{\frac{1}{3}} \quad (1)$$

Where P is the pressure applied, C is material elastic modulus A is the sensing area, AFO is the initial area fraction when P=0, and alpha is a fiber distribution factor in the fibrous assemblies.

The sensor device capacitance exhibits a linear relationship with the contact area (i.e., increasing the sensing area would result in a higher capacitance) and the unit-area capacitance, which is determined by the ionic species, electrode topologies, and temperature. Material elasticity also influences device sensitivity, i.e., a smaller elastic modulus would increase device sensitivity. In addition, the material initial area fraction influenced device sensitivity such that a smaller initial area fraction leads to a larger area fraction increase under pressure to achieve high pressure-capacitance sensitivity. The sensing function relies on the interfacial EDL capacitive layer to achieve ultrahigh mechanical-to-capacitive sensitivity and substantial immunity to ubiquitous capacitive noises from both the body and the environment in a highly flexible package.

The iontronic sensing mechanism utilizes the ionic sensing material with high unit-area capacitance (i.e., consisting high-density mobile ions) that is also structurally, highly elastic (with large area fraction variation) and has a reliable mechanically built form while still maintaining contact with the conductive surfaces. For the intended wearable applications, applying existing fabric materials as substrates simplifies the challenges on both wearability and adaptability. To achieve the desired Iontronic sensitivity, a highly iontronic nanofibrous film was used as the sensing layer by electrospinning an ionic material with high ion concentration and porous structure, which provides a high surface area variation for EDL capacitance change and mechanical robustness from nanoscopic linkages. The ionic conductive material is a gel-based matrix on poly(vinylidene fluoride-cohexafluoropropylene) P(VDF-HFP), with its ionic component of 1-Ethyl-3-methylimidazoliumbis(trifluoromethylsulfonyl)imide [EMIM][TFSI]. Because of the high tensile strength property of P(VDF-HFP), the ionic gel material is applied in a continuous nanofibrous form by electrospinning that evolves into a nanofibrous film. The with several weight ratios of P(VDF-HFP):[EMIM][TFSI] May range from 2:1 to 1:1 to 1:2, in which both the matrix and ionic components were dissolved into a solution phase by an organic solvent, dimethylformamide (DMF), for electrospinning. The weight ratio between P(VDF-HFP) and DMF was maintained at 1:10 for all combinations. Optional compositions as alternative to TFSI include but are not limited to diethylmethyl (2-methoxyethyl)ammonium bis(trifluoromethylsulfonyl) imide, 1-Ethyl-3-methylimidazolium tetrafluoroborate, 1-Hexyl-3-methylimidazolium bis(trifluormethylsulfonyl) imide, 1-Butyl-1-methylpyrrolidinium bis(trifluoromethyl), 1-ethyl-3-methylimidazolium bis(trifluoromethylsulfonyl) imide ([EMIM][bis-TFSI]), 1-butyl-3-methylimidazolium hexafluorophosphate ([BMIM][PF 6]), and 1-ethyl-3-methylimidazolium n-octylsulfate ([EMIM][OctOSO3]).

As described in the various embodiments disclosed below, the sensor device element of the sensing assembly has two essential types of materials to achieve the sensing function: 1) an ionic material and 2) an electrode material. A separate structural material is an optional component of the sensor assembly in addition to the electrode material and the ionic material in the sensing device Ionic material should contain free mobile ions and be electrically conductive. Such as ionic gels (PVDF-HFP/[EMIM][TFSI], PEG/[EMIM][TCM]) and ionomers (Nafion

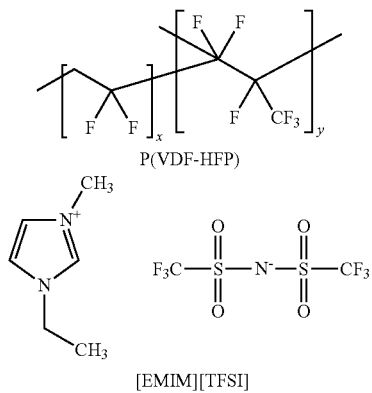

Conductive electrode materials are comprised of: 1) metal and metal liquids, such as gold, aluminum, copper, silver, and their related alloys (ITO), gallium-containing liquid metal, mercury, etc.; 2) Nano-structured state of different metals mentioned above (NanoWire, NanoTube, nanoparticles); 3) organic conductive material, such as graphene, carbon black, carbon nanotubes, conductive polymers (poly (3,4 ethylenedioxythiophene): polystyrene sulfonate (PEDOT:PSS), polyaniline (PANI), and poly(3-hexylthiophene-2,5-diyl) (P3HT)); or 4) conductive fabric such as woven stainless steel, copper coated polyester mesh, and stretchable silver coated polyester. Structural substrate materials preferably have the property of being bendable, elastic, stretchable, foldable and washable. For example, structural material can be TPU, silicone, rubber, conductive fabric, ionic fabric, non-conductive fabric, or a composite of these materials that serves as structural component in the overall sensor assembly. The structural substrate material can also act as a spacer between the electrodes and the ionic material thus changing the sensor pressure range and other sensor properties.

Referring to FIGS. 2A-F, scanning electron microscope (SEM) images of the nanoscopic fibrous morphologies of the electrospun iontronic nanofabric are shown for different composition ratios. Referring to FIGS. 2A-F, the average sizes of the fibrous structures were 176, 147, and 142 nm in diameter for the weight ratios of P(VDF-HFP):[EMIM][TFSI] of 2:1, 1:1, and 1:2, respectively. The same polymer concentrations of the electro-spinning solutions, electrifying voltage, and pumping rate was applied to investigate the effect of ionic concentration. A higher ionic concentration results in a higher conductivity of the pre-spinning solution, giving rise to the formation of thinner nanofibers. Although the size of the nanofiber does not directly contribute to device sensitivity, pursuant to Equation (1) above, the ion concentration, initial area fraction, and elasticity of the ionic material are critical to device performance.

Figure 3A:
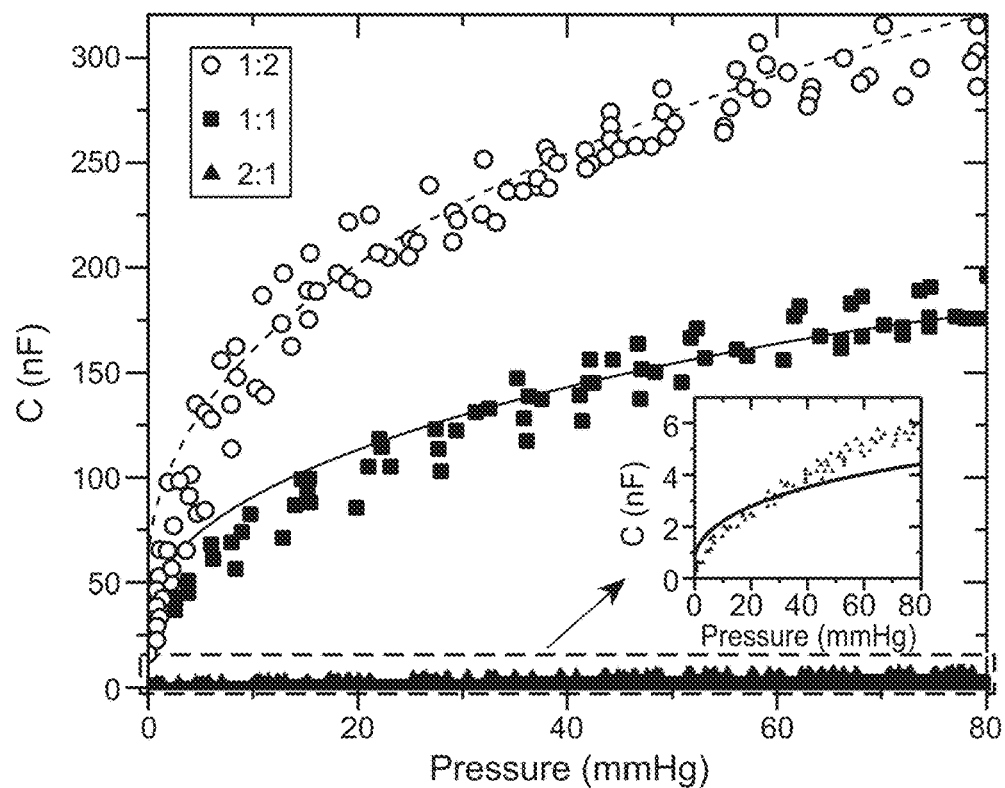
FIG. 3A-3E illustrate performance characteristics of the sensor assembly.
Figure 3B:
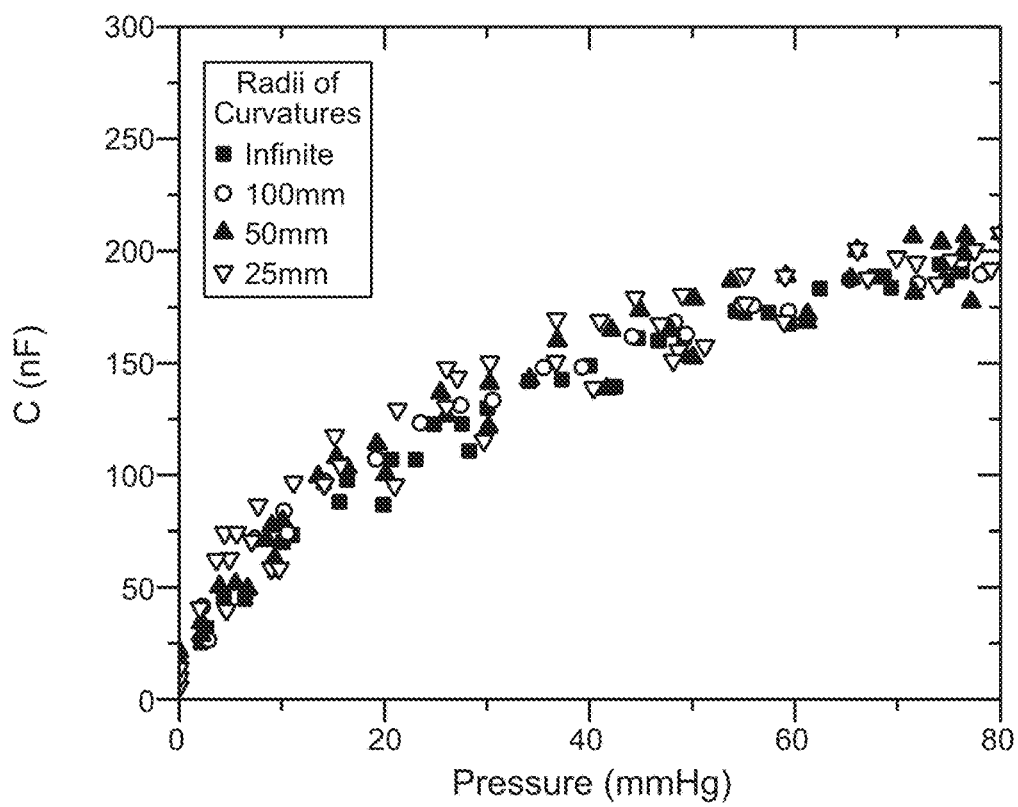

Referring to FIGS. 3A-3E, the performance characteristics of the sensor assembly can be summarized to demonstrate the performance characteristics of the device and to quantitate the mechanical-to-capacitive pressure characteristics that can be sensed by the sensor assembly. FIG. 3A shows plots of the experimental and theoretical all-fabric device sensitivity with the measurement results plotted as dots and the sensitivity predicted by the theoretical model shown with solid lines. In FIG. 3B, the device sensitivity is measured under different radii of curvature, changing from 25, 50, 100 mm to infinite (flat). The mechanical response of an all fabric sensor assembly with an ionic material comprised of P(VDF-HFP):[EMIM][TFSI] 1:1 wt % is shown under varying periodic stimuli of 3C) 1, 3D) 10, and 3E) 25 Hz, respectively.

To allow custom tailoring of certain performance parameters, the ionic and conductive fabrics with a supercapacitive sensing interface as illustrated in FIG. 1a were tested with varying compositions. FIG. 3a summarizes the mechanical-to-capacitive characteristics of the different nanofabric supercapacitive sensors with a fixed sensing surface area of 5×5 mm2 where experimental measurements of the interfacial capacitance are shown as a function of pressure loads (shown in dots) together with theoretical predictions (plotted in lines). Various device sensitivities were calculated and measured with the change of the weight ratios of P(VDF-HFP):[EMIM][TFSI]. In particular, the Nanofabric with 2:1 wt % of P(VDF-HFP):[EMIM][TFSI] had an average pressure sensitivity of 1.05 nF kPa 1 below 15 mmHg, which reduced to 0.421 nF kPa 1 from 15 to 80 mmHg, whereas the nanofabric with a composition of 1:1 wt % had sensitivity values of 38.3 and 11.0 nF kPa 1 in the same pressure ranges, respectively.

Moreover, the nanofabric with higher ionic contents (1:2 wt %) exhibited a highest sensitivity of 114 nF kPa 1 below 10 mmHg, but decreased to 14.8 nF kPa 1 for a higher pressure range (10-80 mmHg). Through the mechanical modeling of the ionic sensing architecture, the pressure-to-capacitance relationship followed approximately a cubic pattern. In the theoretical model, elastic moduli of the P(VDF-HFP):[EMIM][TFSI] ionic polymers were determined experimentally from 61.6, 24.6, and 5.6 MPa, as the composition ratios were changed from 2:1, 1:1, to 1:2 wt %, respectively.

The composition ratio of P(VDF-HFP):[EMIM][TFSI] plays an important role in the performance of the all-fabric sensing devices. The mixing ratio affects the size of the nanofibers and also impacts their mechanical and electrical properties of the sensor assembly by influencing the compression behavior of the nanofiber and the unit area-capacitance of the iontronic interface. A higher ionic content in the supercapacitive nanofabric creates a higher sensitivity in the pressure assembly. To explore the bending influence in more detail, device sensitivity has been characterized while the sensing array has been deformed over surfaces with various radii of curvatures. Device pressure-to-capacitance responses on different radii of curvatures have been compared against performance on planar surface in FIG. 3b. Minimal variations (less than 4%) on the device sensitivity have been observed during the tests, suggesting the all-fabric pressure sensing device has a reliable performance in wearable applications with various surface topologies.

Figure 3C:
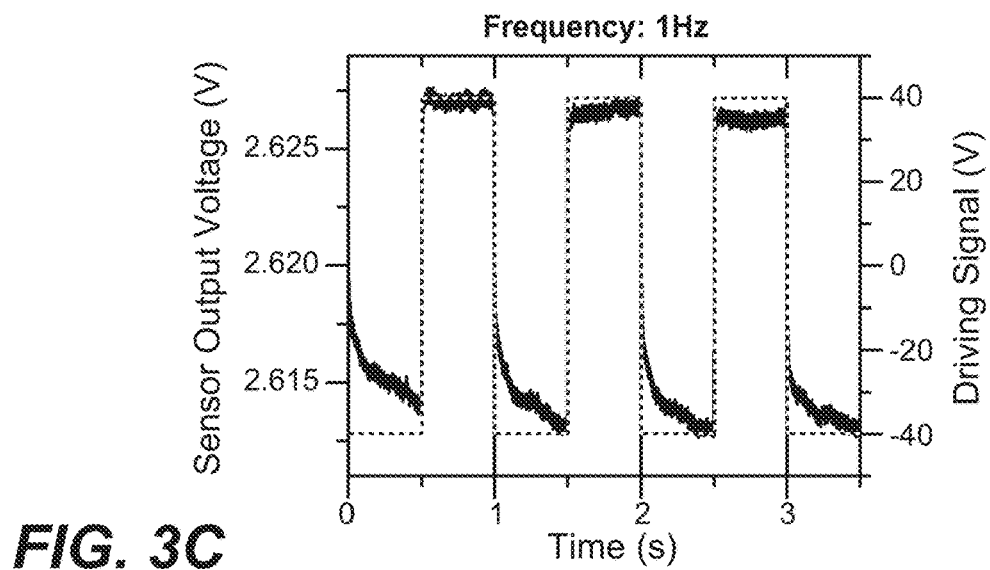
Figure 3D:
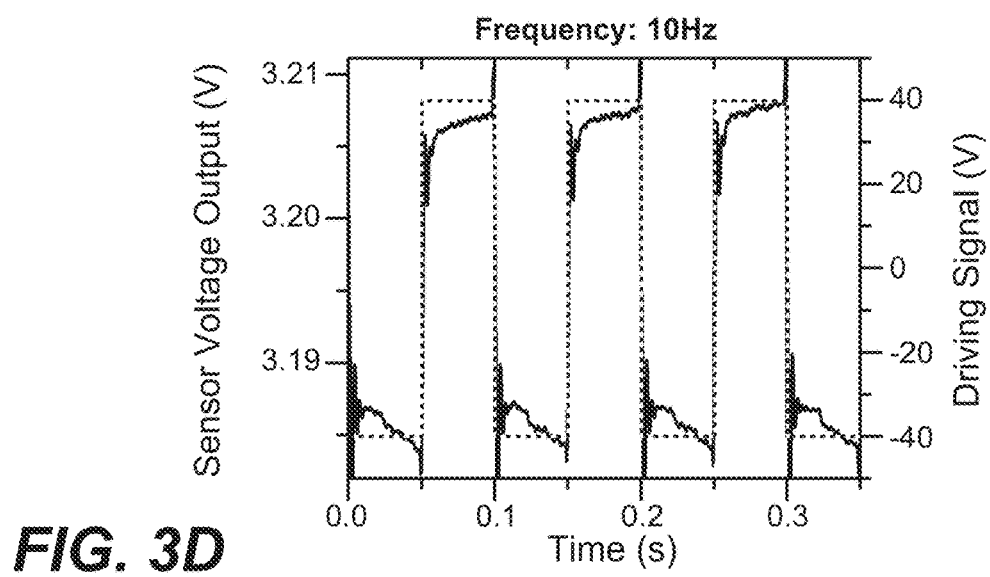
Figure 3E:
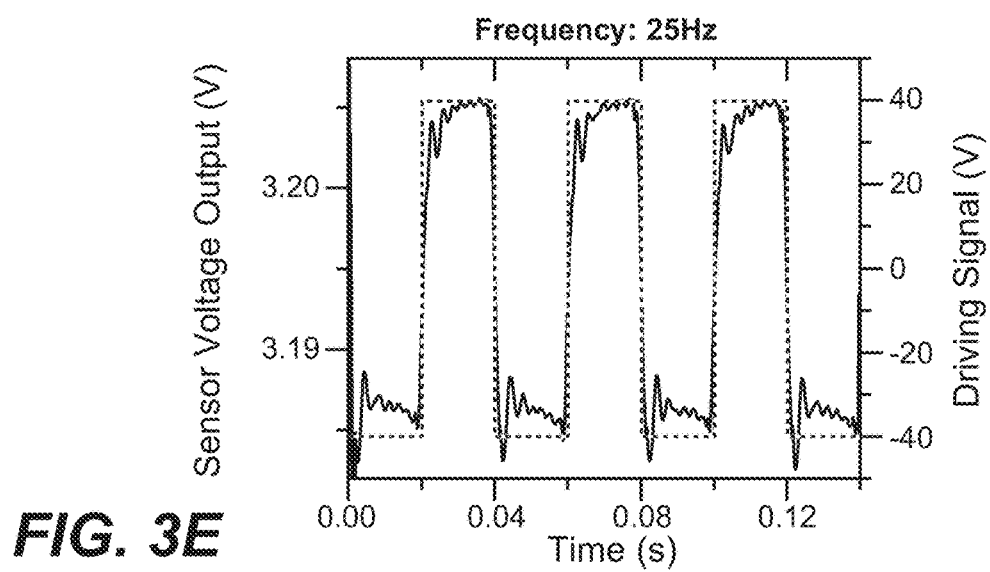

The mechanical response time is also a critical factor for sensors to handle rapid external stimuli. To test the capability of the present sensor assembly, a periodic mechanical load was provided by a piezoelectric actuator driven by square wave signals and then applied to a single sensing unit of a 4×4 nanofabric matrix. The sensor capacitive readout is sampled at 5 kHz by an acquisition circuit. As shown in FIG. 3c-e, when the periodic load is applied at the frequencies of 1, 10, and 25 Hz, the sensing outputs generally follow the same shapes as that of the driving signals, showing a minimal delay and hysteresis. A response time of 4.2 ms is achieved based on the upstroke response readout signal in FIG. 3e, suggesting that the all-fabric supercapacitive sensors can reach a millisecond response time, which can be highly advantageous for monitoring high-frequency body mechanical signals, such as blood pulse To demonstrate the sensitivity and extended wearability, of the sensor assembly, the assembly was incorporated into several wearable pressure monitoring scenes, such as facial pressure mapping as a facemask, gripping pressure mapping as a glove, and radial arterial pressure monitoring as a sleeve. Based on the performance by these devices, a wide range of other constructions can be designed based on the demonstration of the principal operation of the sensor and the performance of the platform sensor assembly in assembling data for healthcare and biomedical applications.

Example 1—Wearable Assemblies

Footwear—

In a particular example of a foot-related or shoe-based sensor assembly, body contact pressure sensors assemblies placed on the bottom of the foot or surrounding the foot and ankle to measure the force and force profile created by any walking, standing, running or jumping action taken by the wearer. Detection of force exerted by a step or pattern of steps yields data that can be used to assess movement patterns, gait parameters, posture and an overall activity level, including steps and force expressed as a unit measurement or as a summation of data over time, including, separate sensors isolated for different parts of the foot, data analytics that isolate regions of the foot separately as well as isolating pressure measurements for each of a left foot and a right foot independently or together, and a comparison of the force or force profile exerted by each foot or by both feet together.

Measurement of cardiac effects are also readily made by sensors incorporated into footwear. The dorsalis pedis is the major artery the top of the foot and has a pronounced pulse signal. As with any pulse, pressure, or other cardiac effect measured pursuant to the sensor assembly of the invention, these data can be obtained from sensors mounted proximate to the dorsalis pedis and can be coordinated with other sensors surrounding the feet and ankles or combined with other sensors placed anywhere on the body. The individual or combined force measurements at each foot may be correlated to pulse, respiration or overall activity level using data gathered from a sensor array comprising individual or multiple sensor assemblies as described herein or in combination with other conventional sensor assemblies. Sensor assemblies associated with footwear can be disposed within a shoe, such as underneath the soul cushion or superior to the foot between the foot and the tongue of tissue. Because of the low profile of the sensor assemblies described herein, the sensor assemblies do not interfere with the ordinary function of the shoe and can be readily incorporated as a separate sensor mechanism without altering the construction of the companion shoe.

Further, and as is shown in FIG. 1B, the companion shoe, as with any other garment or wearable construct described herein may alternatively be constructed to have the fabric sensor assembly permanently incorporated as part of the finished article or may be fitted with a pouch or other enclosure that receives the fabric-based sensor assembly in a dedicated housing or pouch. Because sensor assembly is incorporated into fabric, the sensor assembly is flexible and easily manipulated by hand to locate the sensor assembly against any part of the body or within an article of clothing as desired.

Figure 4A:
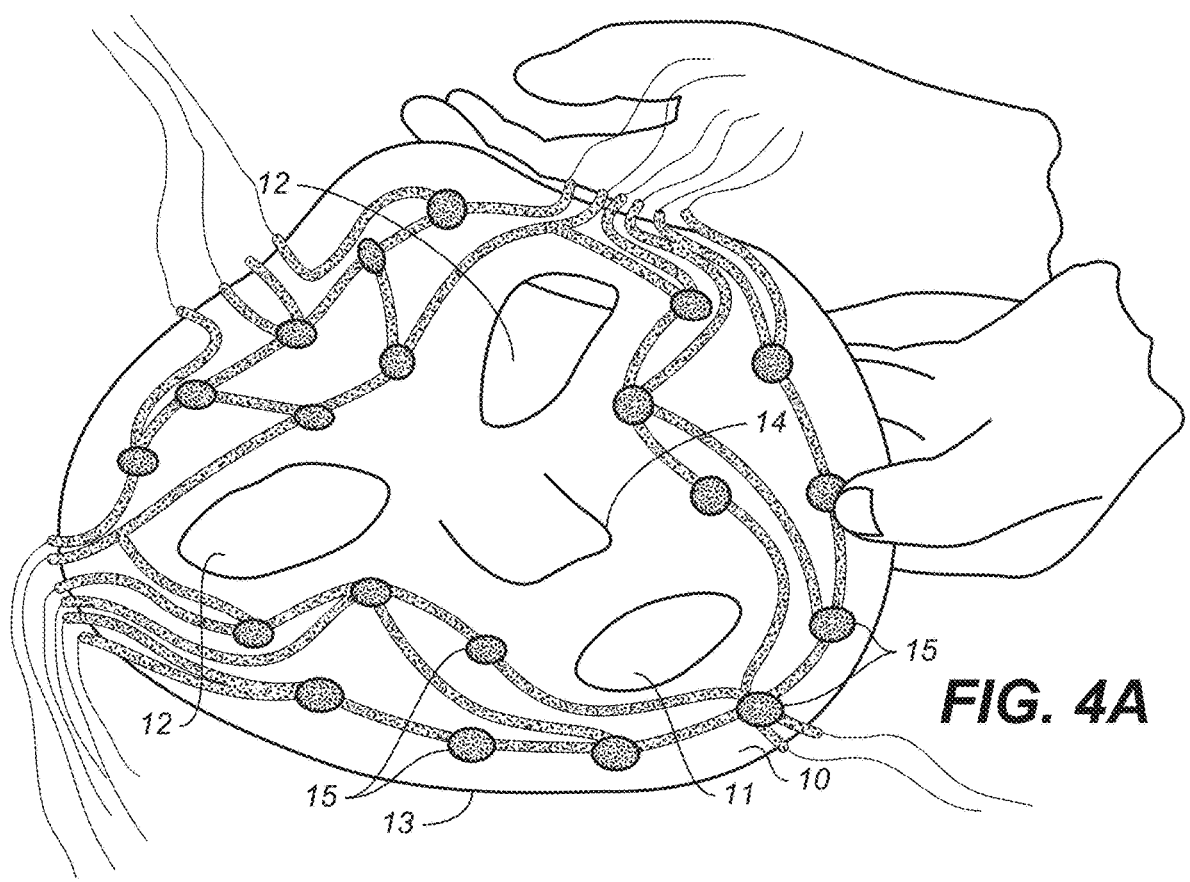
FIGS. 4A-4H. a)
Figure 4B:
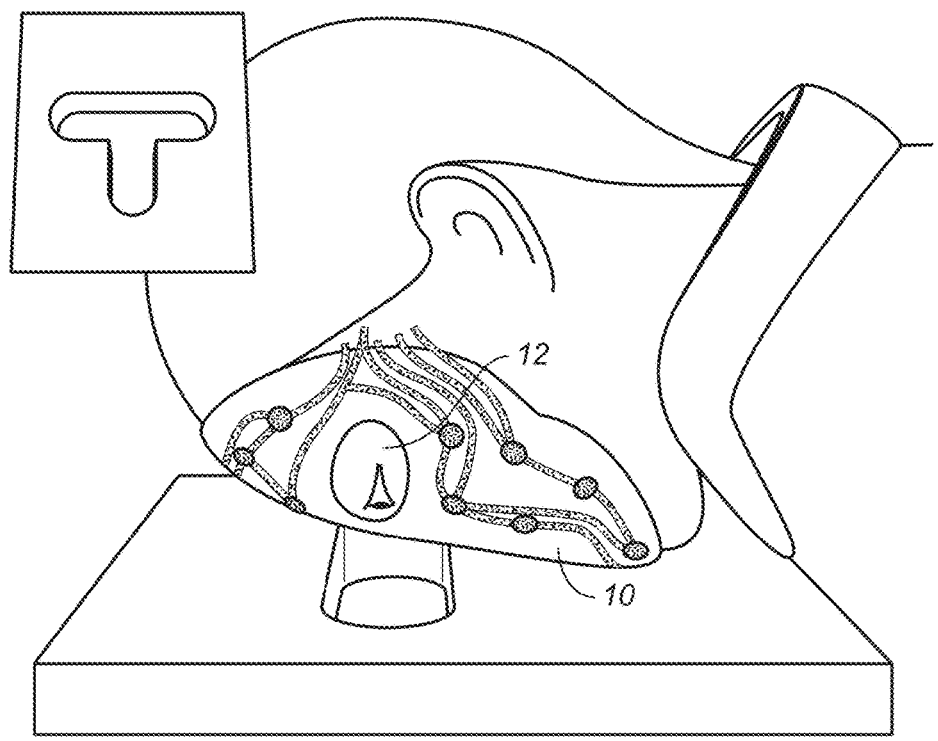

Head and Neck Based Sensor Assemblies—The sensor assemblies can be manufactured as a plurality of individual sensors disposed in an array that is uniquely oriented to conform to the shape of any portion of the human body. An example of such construct is shown in FIGS. 4A and 4B wherein an array of sensor assemblies is incorporated into a woven fabric facemask made from silk threads (FIG. 4A) for pressure mapping of facial skin. Neurosurgeons and anesthesiologists closely track facial pressure distribution for spinal surgery patients over prolonged procedures in a prone position due to the potential for skin damage and pressure ulcerations. Clinically, pressure ulcers can evolve with a prolonged exposure (more than 2 h) to a high pressure loading (greater than 32 mmHg) area particularly when patients are immobilized under anesthesia do not not receive any tactile feedback from the uncomfortably high pressure caused by head and body weights.

Figure 4C:
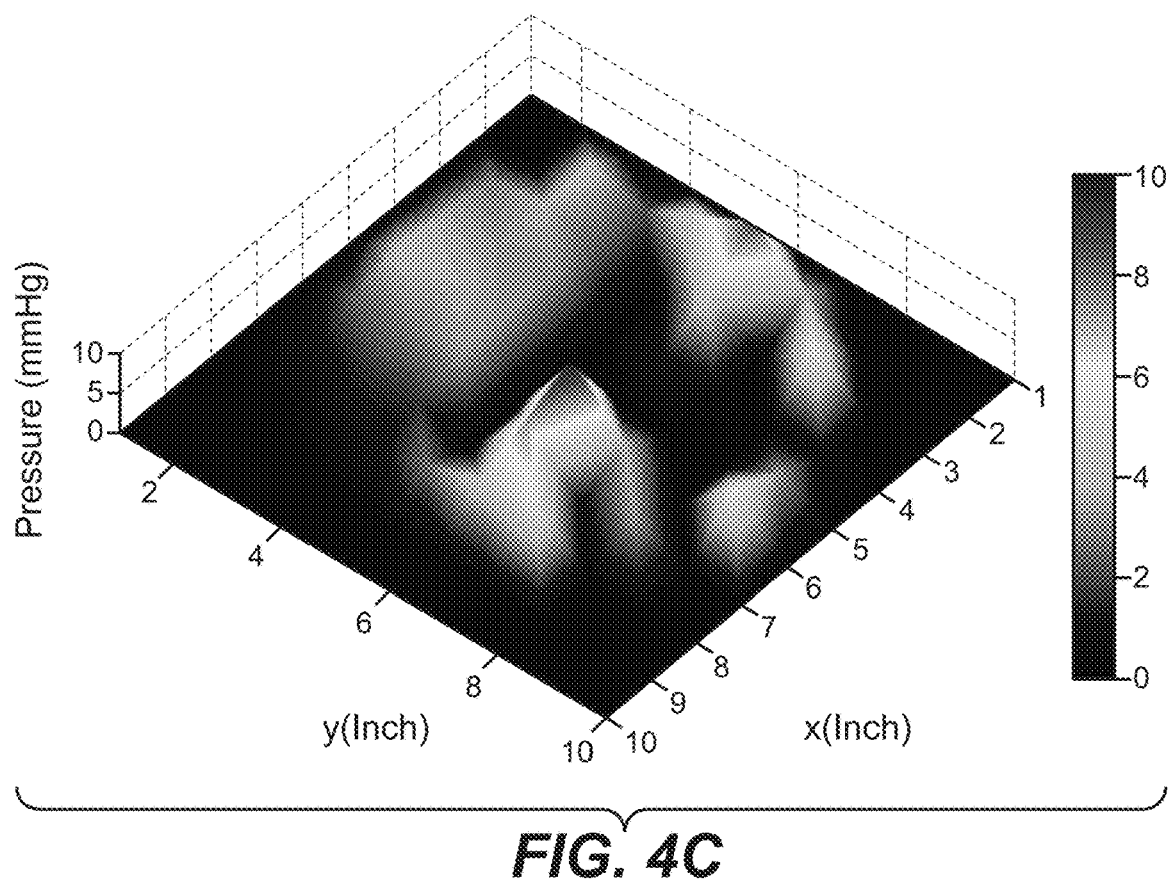

In these types of prone-positioned surgeries, a head-positioning foam with a T-shape cut (CF-1007DH, Soule Medical) is typically used, leaving the eyes and nose suspended and endotracheal tubes with external connections in clinical settings, as shown in FIG. 4A-4B. Correspondingly, the facemask with a plurality of embedded sensor assemblies disposed at selected detection points, are organized in a matrix located at potential pressure-concentrating areas, including the forehead, both cheeks and chin areas, where a thin skin layer lies above a bony prominence. Each sensor assembly has a P(VDF-HFP):[EMIM][TFSI] 1:1 wt % formula and each assembly has an effective circular-shaped sensing area of 4 mm diameter. FIG. 4C shows the measured facial pressure distribution of a healthy volunteer when lying onto the foam positioner in a prone position (FIG. 4B). As seen, both of the cheek areas of the test subject experience a high pressure concentration of 10 mmHg compared to other facial locations.

Figure 4D:
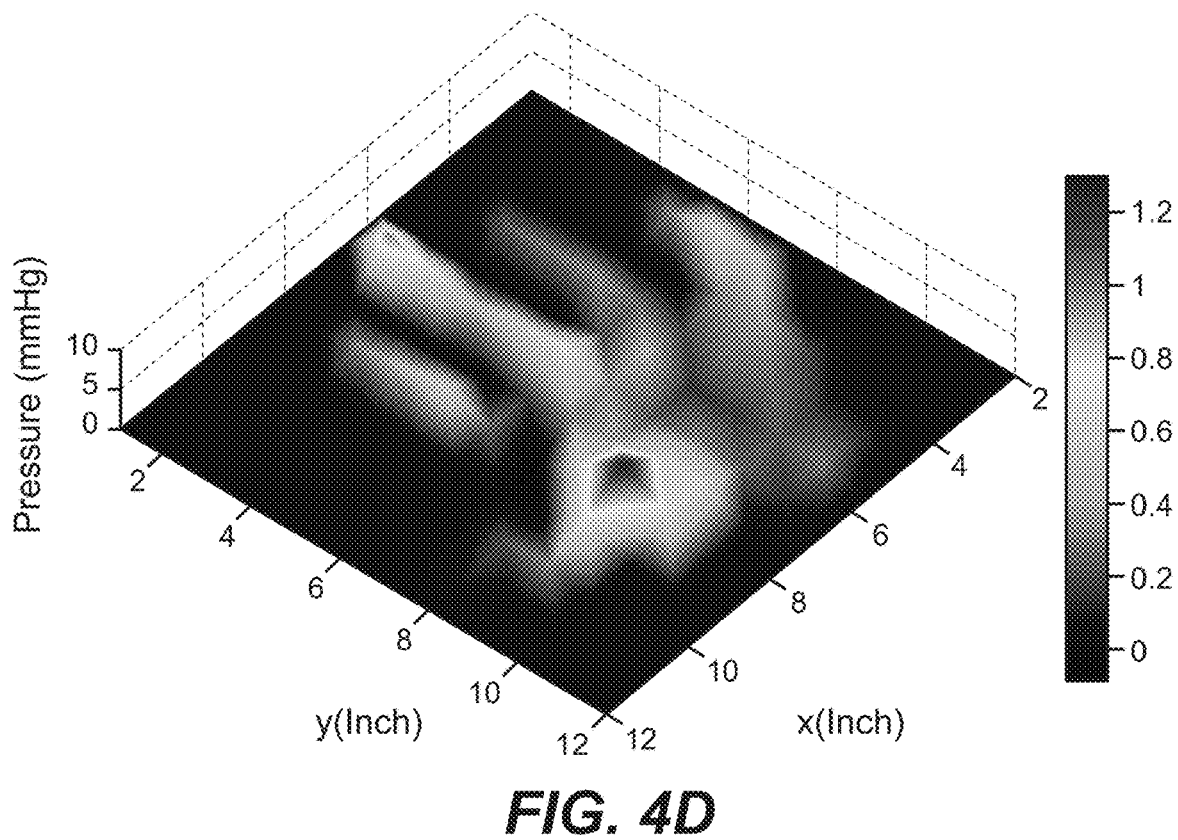

Accordingly, the invention includes a platform having sensor assemblies disposed therein and pre-configured to conform to a specific contour of an area of the human body, optionally a companion structure designed to exert pressure over the substantial portion of the sensor platform in order to enhance the contact between the sensor assemblies and the human body. The invention also includes a pressure profile that is unique to the specific region of the body and to the resulting pressure data such that a visual pressure profile, as shown in FIGS. 4C-D, is the result.

In this particular embodiment, by receiving accurate pressure data from the face of the prone patient, patients in prone-positioned surgeries can be positioned and repositioned in response to continuous tracking data from the sensor assembly that may, for example, warn of an extended concentrated pressure load on the face. In response to examination of the pressure profile, and potentially comparison to a normal pressure profile, the clinician nd can reposition the patient specifically in response to positions of extended high pressure as identified by the sensor platform.

Additionally, as noted above, the pressure platform can be combined with other input measuring separate physiological parameters. In this embodiment, an example would be correlation of the pressure mask with a pulse signal. Each of the carotid, jugular, and temporal arteries are located around the face and are a ready source of a pulse signal that is measured and a heart rate calculated based on the pulse waveform signal. Both the pressure and the pulse measurements can individually or collectively be coordinated with other measurements, including respiration, movement and hemodynamic parameters obtained from other body sites.

For the jugular artery in particular, a tie or necklace is an unobtrusive way to incorporate a sensor assembly into a common, existing item of clothing that typically is comprised of a fabric constituent. With this embodiment, as with the foam companion device of the facemask, application of a separate forces causes the sensor assembly to stay in close conformity with the target area the body. In the case of the neck or other portion of the body, force can be applied from the elongation of an elastic component, or from stretching action of the fabric constituent containing the pressure assemblies. In one embodiment, the sensor assembly has a series of fixed circumferential dimensions and a companion device that tightens the sensor assembly around the target site of the body to apply force to the sensor assembly to maintain close engagement between the sensor assembly and the skin.

The sensor assembly may be incorporated into a variety of known garments or structures that our pre-designed to provide close conforming engagement to the skin. For head and neck applications, a single sensor assembly or an array of the sensor assemblies may be attached to the cranial region by incorporating one or more sensor assemblies into a hat, helmet, or headband. Preferably, the backing side of the sensor assembly further comprises, or is comprised of, a flexible fabric band or construct containing a flexible fabric band, together with an adjustable tension band or fixed sized material. As with a necktie, force is advantageously applied from tension caused by an elastic or binding structure incorporated into the hat or headband. In this configuration, the sensor is on the innermost portion of the assembly and the remaining structures facilitate a static or dynamic pressure being asserted against the head to maintain close configuration between the sensor and the skin.

Forearm, Wrist, and Hand Based Sensor Assemblies—

Figure 4E:
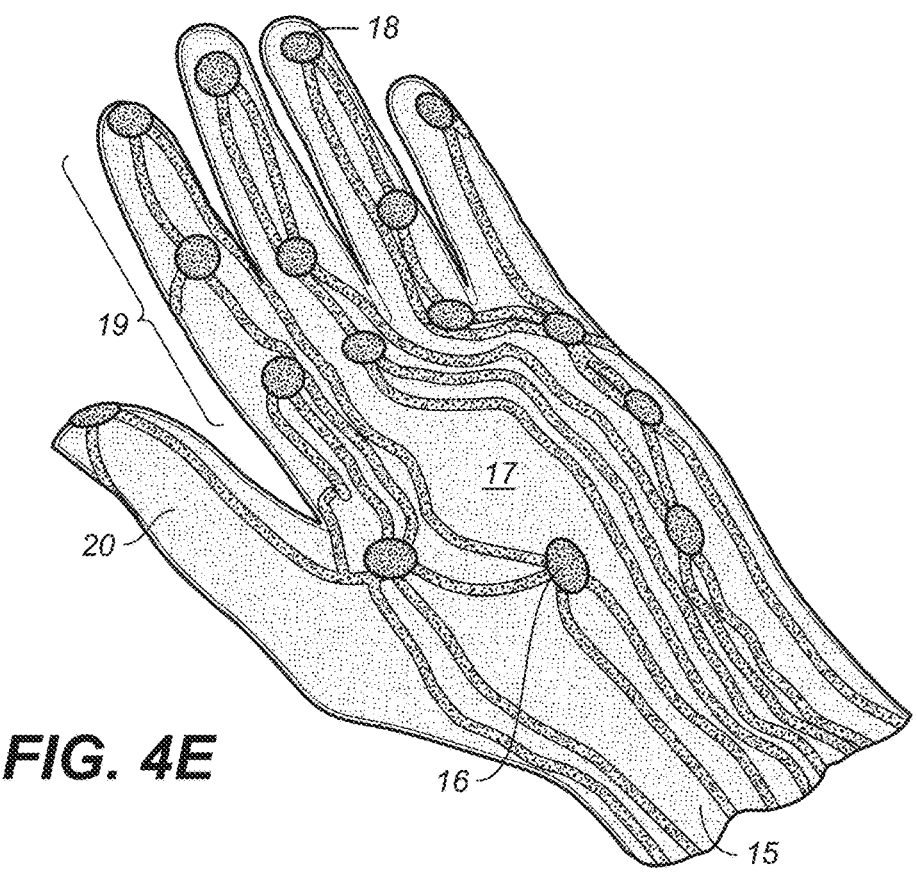
Figure 4F:
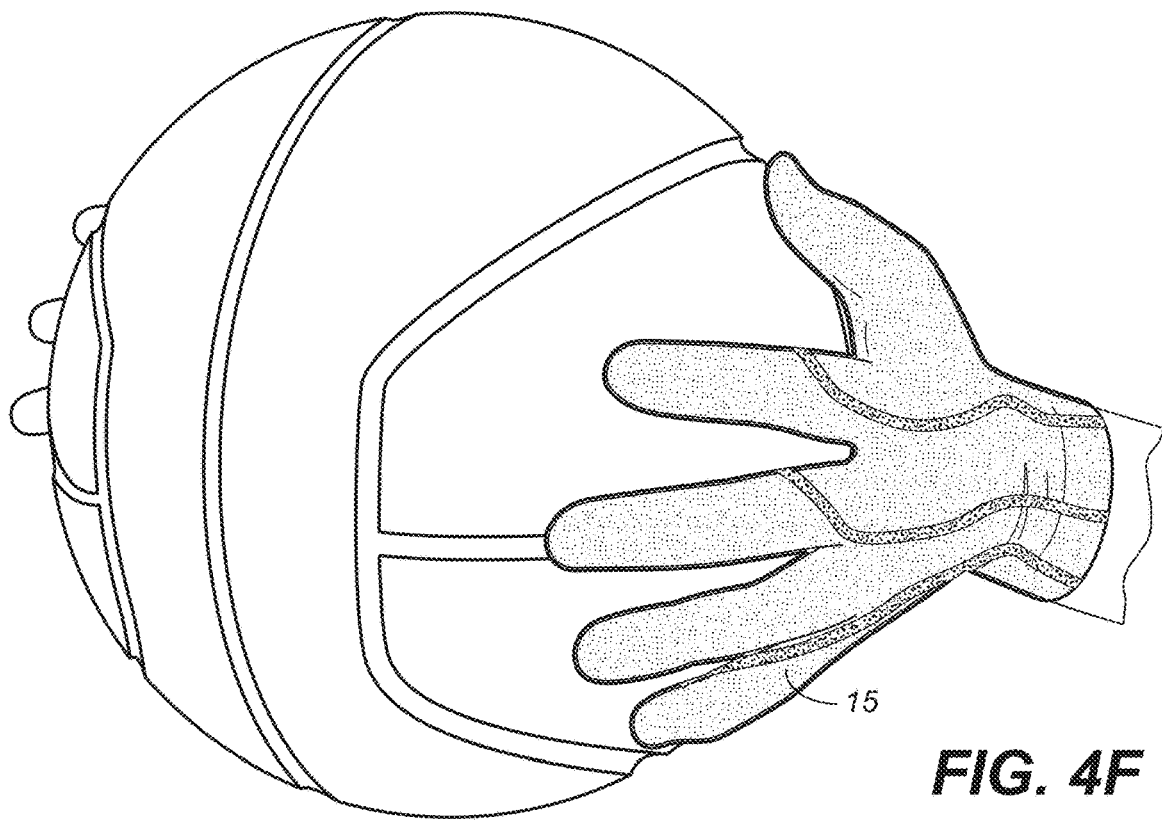

A sensor assembly is also used to dynamically measure hand gripping pressure and pressure distribution by integrating a sensing matrix or array into gloves. Referring to FIG. 4E, nanofabric sensing units on the gloves were constructed in an array about the fingers and palms. The array may be random or ordered for data processing. In one embodiment, a 4×4 sensing matrix yielding an effective square, rectangular, or circular-shaped sensing array formed of a plurality of sensors with an area of 4 mm in diameter. In this embodiment, the P(VDF-HFP):[EMIM][TFSI] 1:1 wt % formula was used. Referring to FIG. 4F one or a pair of pressure sensing gloves are used by a player holding a basketball. The sensor assemblies incorporated. into the gloves yield a high sensitivity, fast-response time sensing matrix that provides a pressure distribution map with hand and finger position together with gripping force data that is successfully resolved in a real-time and with high-resolution, including the ability to resolve pressure differentials between 0-1.4 mmHg and including both planar and curved configurations.

Figure 4G:
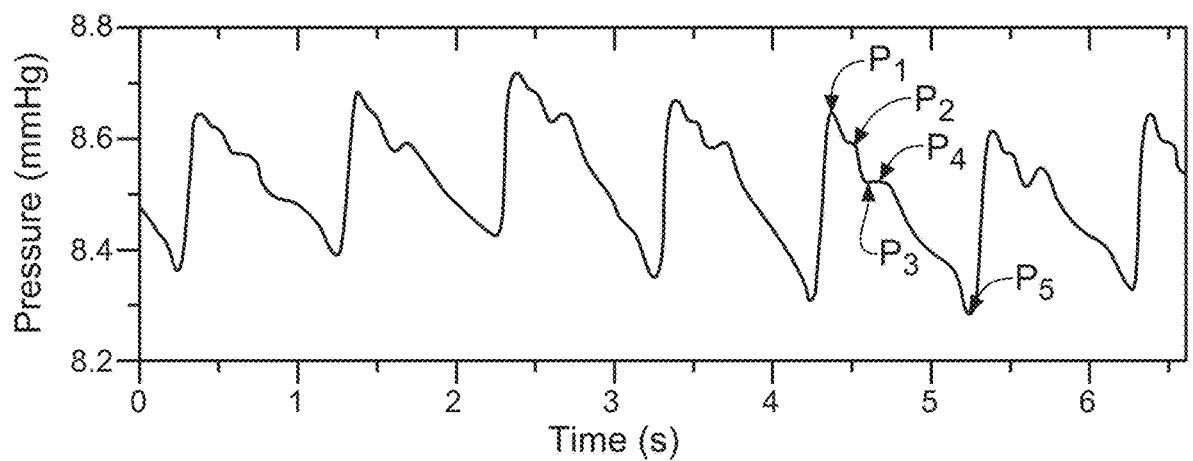

In addition to wearable measurements of various interface pressures, the fabric based sensor assemblies can be applied to cardiac events, including real-time radial arterial pulse waveform monitoring. FIG. 4G shows pulse pressure waveform datapoints that can be obtained from a sensor assembly affixed to the wrist as shown in FIG. 4H or any of the other arterial pulse access points as described above.

Figure 4H:
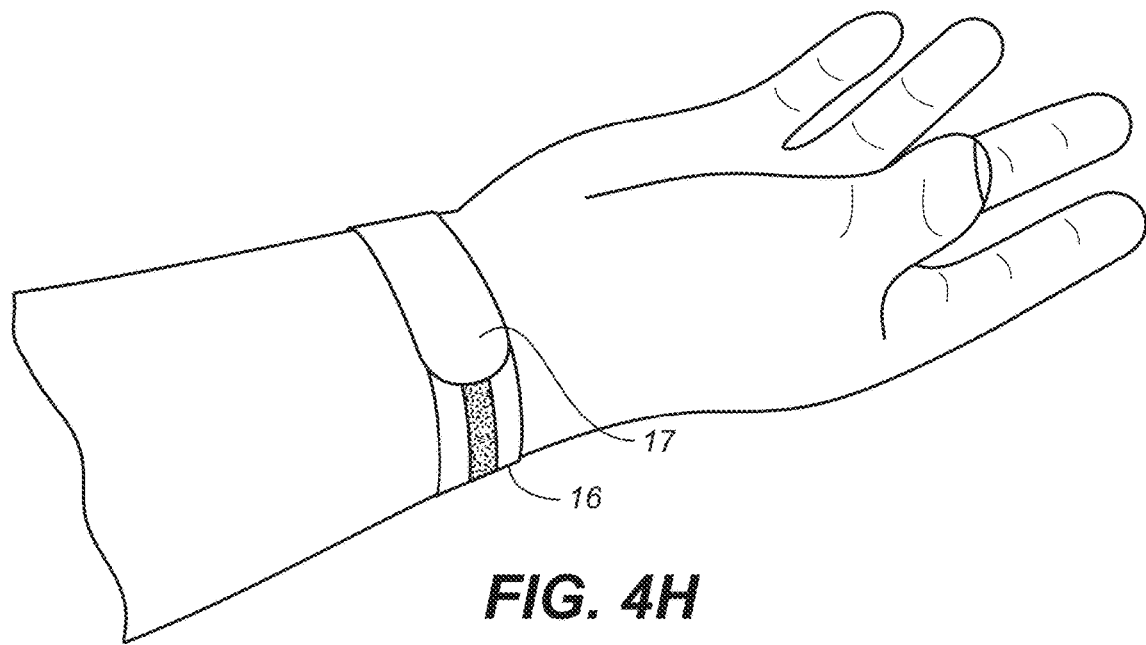

In the example of FIGS. 4G and 4H, pulse signals were obtained and recorded from a 28-year-old healthy volunteer wearing the all-fabric sensing wrist band of FIG. 4H, and having an effective sensing area of 5×5 mm2 an fabricated with the P(VDFHFP):[EMIM][TFSI] 1:1 wt % nanofibrous layer as described above. As is illustrated in FIG. 4G, important data points are be determined from the recorded signals of the radial arterial pressure variation, the detailed waveform features can be resolved by and extracted from the nanofabric sensor, which includes systolic peak (P1), reflected systolic peak (P2), dicrotic notch (P3), diastolic peak (P4), and end-diastolic pressure (P5). According to the measurements, the pulse pressure (P5 P1) that is transferred to the skin surface presents lower than 0.34 mmHg (45 Pa), under a low level of compression pressure (8.4 mmHg) applied to the wrist by the band. By further numerically analyzing the continuously tracked pressure waveforms, additional pertinent hemodynamic parameters can be quantitatively evaluated in real-time, such as augmentation index (AI=(P1 P5)/(P2:P5)) and reflectance index (RI=(P1:P5)/(P4:P5)). Notably, the pressure difference between points P1 and P2 is resolved at 0.06 mmHg (8 Pa), whereas that between points P3 and P4 is recorded at 0.018 mmHg (2.4 Pa). Such delicate resolutions on the weak pulse pressure waveforms reconfirmed the single-Pascal resolution of the supercapacitive all-fabric sensors, despite the extremely noisy body environments for capacitive readings. Sensor assembly contact with any area of skin proximate most subdermal arteries enables detection of at least heart rate, pulse waveform, including a variety of cardiac artifacts detectable from the waveform, and a number of cardiac parameters including individual components of blood pressure.

Chest and Abdomen—Direct measurement of hemodynamic parameters surrounding the heart or available arteries in the chest and torso are also available for locating one or a plurality of sensor assemblies. As with the embodiments described above, the sensor may be attached to the torso or lower body by means of the separate band tightly attached around the body or by incorporating the sensor is assembly into existing clothing articles such as underwear or a brassiere. Also as with the above embodiments, a preferred method of maintaining engagement between the sensor assembly and the skin is by the addition of a separate construct that holds the sensor assembly of the skin and may have an elastic element or other typical feature for adjustable tension, such as a belt or other common expedients such as Velcro®.

Example 2—Data Collection, Connection and Display

The electronic circuitry electrically connected to the sensor assemblies detects the change in conductance of the sensor and exports that data for analysis or display. The sensor assembly contains electrodes for transmission of the collected data to a display or data processing unit. Electrical fabric connectors allow features such as washability, water resistance, flexibility, and conformability to be maintained. These connectors can include: mechanically attachable conductors (e.g. crimp-on pins), electrically conductive glues/polymers, and sewn in conductive fibers. The output wire can be oriented as a series or wires or coaxially.

The impedance of the sensor can be measure with the capacitor discharge method, the 4 point probe method, or measure the RMS of a sine wave transmitted through a sensor. This can data can be exported in the raw form or converted into the appropriate mechanical input (i.e. pressure, stretch, or bending) via a calibration curve.

The sensor data can be transmitted through any wired or wireless digital communication protocol, including: Bluetooth, Bluetooth low energy, WiFi, UART, and serial communication. Many data export methods allow for real time monitoring of sensor outputs. Bluetooth low energy allows the transmission of data to many types of devices with minimal power consumption. WiFi communication allows the transmission of data to the internet, the cloud, and distant signal processing locations. Data can be stored directly on the electronics to provide long term, low power monitoring of a sensor.

The displayed signal can be a raw mechanical signal (i.e. pressure, stretch, or bending). This data can be graphed over time, visualized as a heat map, or provide alerts at some extreme value. The display signal can be a filtered/interpreted biosignal. For example, a filtered pulse waveform, heart rate, breathe rate, a recognized gesture, fetal motion intensity, bodily activity level.

Feedback systems can be implemented to provide information about the biosignal being acquired, or about the state of the electronics. For example, an indicator can notify the wearer that a gesture was recognized, fetal motion was recognized, or the pulse is detected. Feedback can act as a biofeedback tool to control the biosignal of interest. One method of feedback is with an optical display. This could include a blinking LED or a graphical display. One method of feedback is with an auditory message such as a sound, tone, or recording.

Example 3—Various Designs for Orientation of Ionic Material, Conductive Material, and Substrate Material Referring to FIG. 5, a cross-section of a sensor assembly shows an embodiment that the is comprised of three component materials: a substrate material 20, a conductive material 21, and an ionic material 22. The height of the construct is defined by the dimensions of the lateral structural substrate material 24 that encloses the conductive material 21 and the ionic material 22, together with the layers of the substrate material 20. The substrate materials 20, 24 forming the layers in contact with only the conducting material layer 21 in the upper panel of FIG. 5 or with both conducting layer 21 and the ionic material 22 in the lower panel of FIG. 5 may be the same material or different material. In this embodiment, parallel fibers 25 are coated with the ionic material 22 and sandwiched between conductive layers 21 substrate material layers 20. The substrate material layers 20 are disposed on either side of the construct comprising the two conductive material layers 21 engaging the outer tangential surface of the fiber substrate 23. In this configuration, the ionic material-coated fibers 25 form an inner middle layer sandwiched by the conductive material 21 layers and the substrate materials 20 and contained by the structural substrate materials 24. In the upper panel of FIG. 5 the conductive material 21 is shown as an intact layer that engages the outer surface of each of the individual ionic material coated fibers 25 along the entire width of the array of fibers 25. As shown in the lower panel of FIG. 5, the conductive material 21 may be formed in separate ribbons that comprise a pattern for separating the measurement of two separate conductive material elements 21 or for creating a pattern in the overall fabric platform in which the sensor assembly is disposed.

Referring to FIG. 6, one embodiment of the device is comprised of, or consists essentially of, two functional layers: one ionic material layer comprised of a fiber substrate 23 coated with the ionic material 22 and disposed in a parallel array of fibers as in FIG. 5, and one conductive material layer that is disposed within a substrate material layer 20, 24 such that the material layer may surround the conductive material layers 21 or may comprise structural substrate material 24. In the embodiment of the upper panel of FIG. 6, patterned conducting layers 21 engage the outer tangential surface of the ionic material at a plurality of discrete regions within the fabric platform. Conductive layers 21 lie in a parallel configuration along the length of their engagement of the array of fibers 25. As shown in the lower panel of FIG. 6, the array of fibers 25 may be contacted along the entirety of a plurality of the individual fibers by a conductive material layer 21 in the absence of a substrate material as a boundary to the conductive material. Additionally, as will be appreciated from all of the figures describing the various design options, the substrate material can be interspersed with the array of fiber layers 25 two surround and provide structural support for the fiber layers or may be oriented in a variety of different configurations depending on the design of the fabric platform. Similarly, the selective placement of structural support substrate material 24 interspersed with substrate material 20 is dictated by the desired flexibility and rigidity of the overall fabric platform. As described above, the conductive material 21 may be disposed as layers that engage all or any portion of the ionic material 22 along any selected portion of the total ionic material area 23. Because the pressure sensor function derives from the engagement of the conducting material 21 and the ionic material 22, the conducting material 21 may be fabricated as a patterned electrode to separate the sensing functions at any point or array of clients to form a sensing area within a fabric platform (see FIG. 1C, FIG. 4A, and FIG. 4D).

Referring to FIG. 7, the conductive material 21 can be fabricated by known techniques as a standalone layer such as by conductive materials woven into a fabric such that no additional non-conductive substrate material need be added to support the conductive electrode material 21. Non-conductive substrate material 21, 24 can be present even where not used to support the conductive material 21 for structural or sealing functions.

Figure 8:
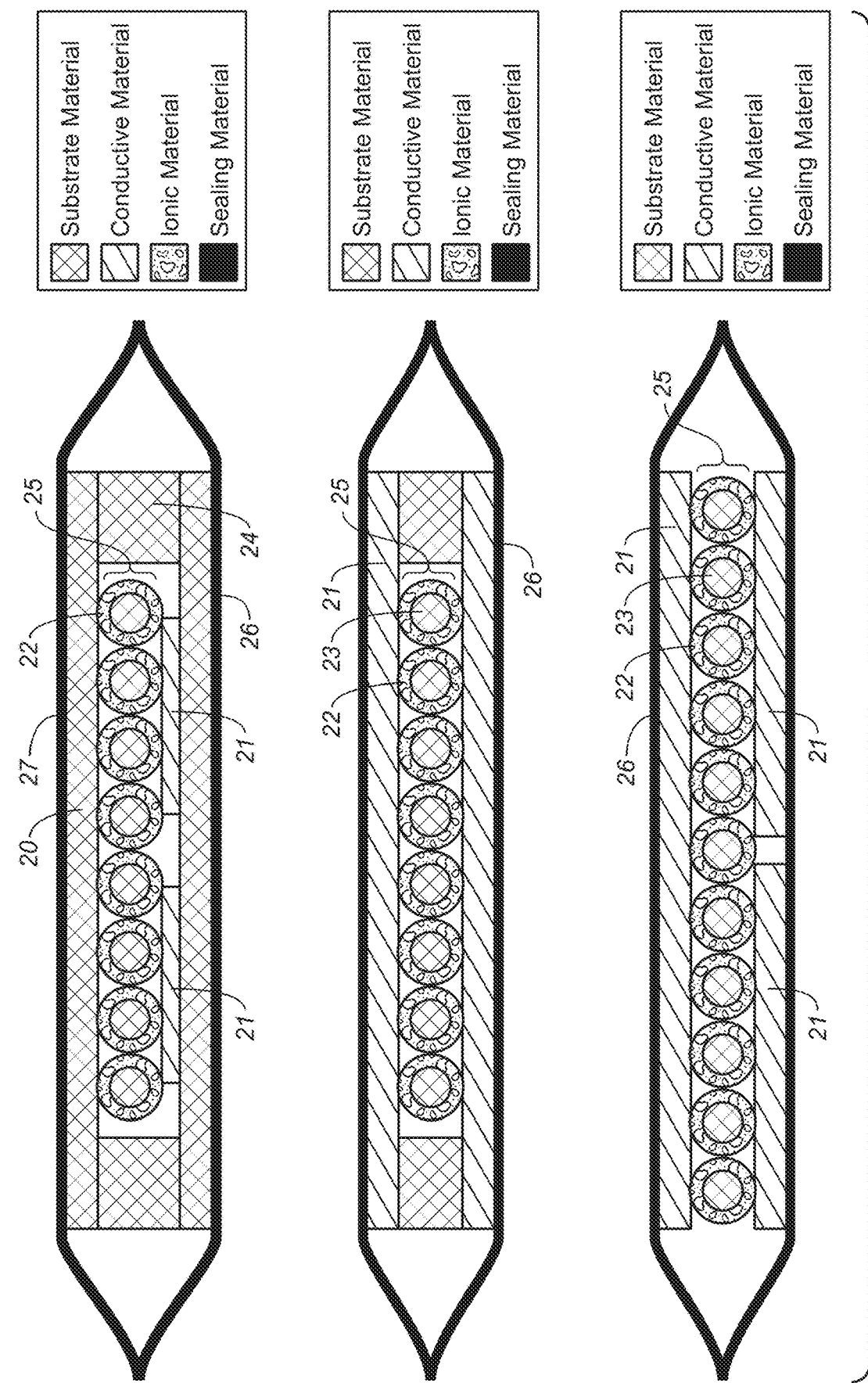
FIG. 8 is embodiments of the invention that are sealed about a periphery thereof to create a fluid or moisture impermeable barrier around the sensing element in the platform structure.

Referring to FIG. 8, a complete, intact and functional sensor assembly can be constructed for moisture or waterproof applications using a variety of seals that adhere to any of the ionic material 22, the conductive material 21, or the structural or non-structural substrate material 21,24. The sealing material 27 can also function to maintain the contact between the ionic material 22 and the conductive material 21 in any of the configurations of FIG. 5, 6, or 7. Suitable flexible seal materials 27 can be attached to the other elements of the sensing assembly using several known manufacturing techniques, including heat bonding, infrared, or ultrasound bonding film to seal the sensor assembly from external moisture and to allow for the sensor assembly to be exposed to moisture or humidity, including from external to the sensor assembly. This addition of the sealing material 27 thereby provides a fabric-based sensor assembly that is capable of being integrated into an article of clothing or an accessory thereto that can be fully submersed and laundered.

Referring to FIG. 9, the sensor assembly may further be comprised of one or more external conducting coating layers 21a, 21b for sensor grounding. In this embodiment, the any portion of the sensor assembly is coated with the external conductive material to reduce parasitic noises and EMF influences. Any combination of structural and nonstructural substrate materials 20, 24 can be selectively placed around the combination of the ionic material and the conductive material to provide any selected design or physical performance parameters for the sensor assembly.

Referring to FIG. 10, in this embodiment, the ionic material layer is comprised of or consists essentially of a porous ionic material. The material forming the porous ionic material layer can be electrospun nanofiber 28 that nanofibrous layer disposed between conductive layers 21 to the porous layer. As described for example in connection with, for example, FIG. 1C, a nanofiber layer can be disposed between conductive fabric layers and bonded by a heat sensitive liner to form an integrated unit that is optionally also formed with non-conductive fabric to create an entire fabric-based platform that is readily integrated into garments, articles of clothing, shoes, or other wearable assembly as described herein.

Figure 11:
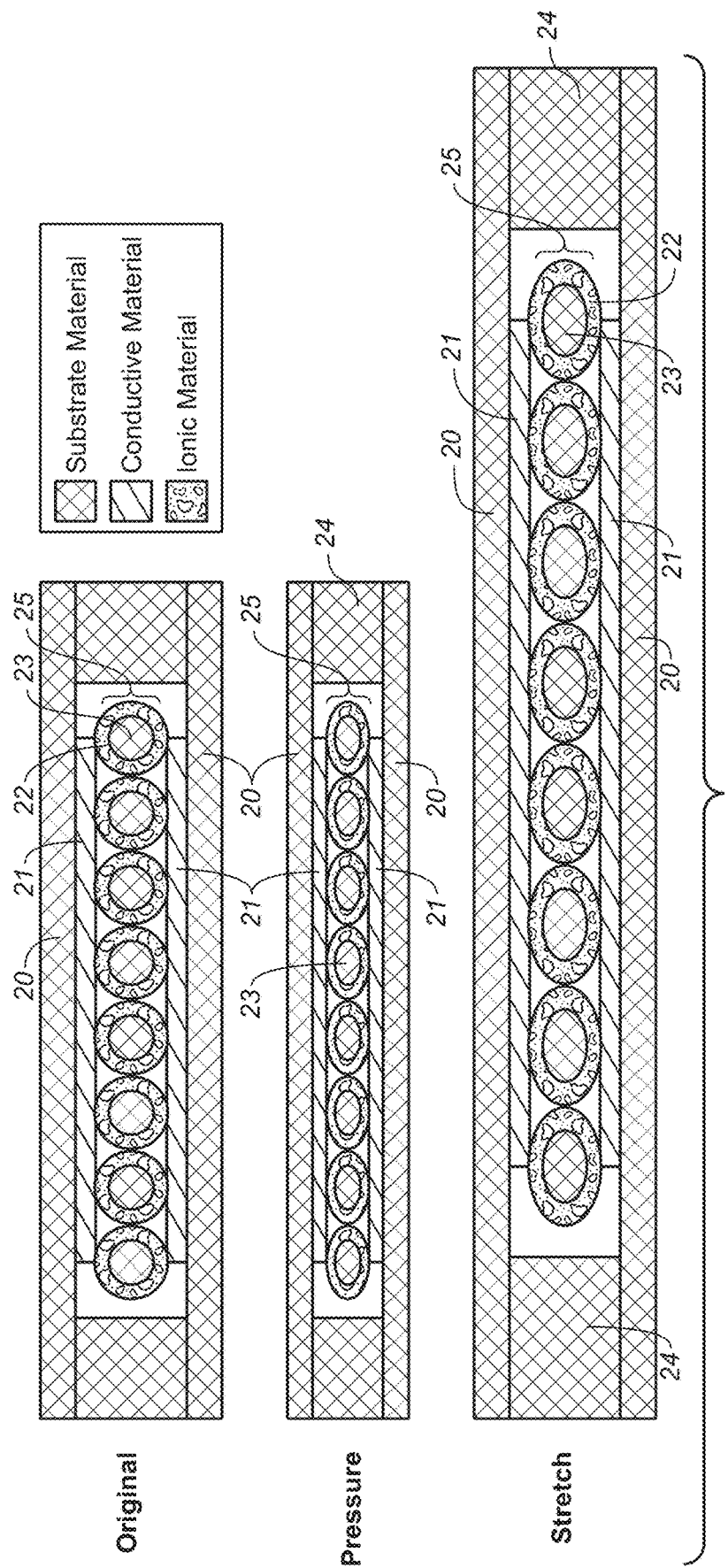
FIG. 11 is an embodiment were each of the substrate material, conductive material, and ionic material elements of the sensor assembly are made with a stretchable material or substrate such that the change in confirmation of the sensor causes a change at the interface of the ionic material and the conductive material to produce a differential readout signal comprised of at least a resistance and capacitance element that reflects the contraction or expansion of the sensor assembly under stretch and sensor deflection under pressure.

Referring to FIG. 11, three different conformational states of the sensor assembly are shown using the example of the embodiment of FIG. 5 (upper panel) as an example of the conformational changes that are experienced by any of the embodiments described herein and where the conformational changes can be used to measure a variety of static and dynamic pressure values. The upper panel of FIG. 11 shows an original confirmation of the sensor assembly having outer substrate material layers 20 supported by substrate structural layers 24 and a pair of conductive material layers 21 and enclosing an array of parallel ionic material-coated fibers 25 comprised of a fiber substrate 23 coated with ionic material 22. As noted above, the conductance values of this configuration is based on the total area of contact between the ionic material 22 and the conductive material 21. In the center panel of FIG. 12, a pressure is exerted normal to the plane of the substrate material 22 compress the sensor assembly in a vertical dimension resulting in a second confirmation having a reduced total height compared to the original confirmation. In this embodiment, the area of contact between the ionic material 22 and the conductive material 21 is altered (in this configuration increased) resulting in a change in the electrical conductance through the conductive materials 21. This change in electrical conductance is measurable and is correlated to a change in pressure. Similarly, depending on the calculation of the change in electrical conductance, a change in the rate of change of electrical conductance can be correlated to a change in the rate of change of the pressure value sensed by the sensor assembly. Referring to the lower panel of FIG. 12, a stretch confirmation results from exerting horizontal forces on the sensor assembly such that the horizontal dimension of the sensor assembly is increased. As with the change in vertical dimension, a change in the horizontal direction alters the contact area of the ionic material 22 and the conductive material 21 in a characteristic fashion that is identifiable as a difference in the horizontal dimension of the sensor assembly rather than the vertical dimension. The device readout signal, including but not limited to measurements of resistance and/or capacitance, reflects the difference between a static or original confirmation and a pressured or stretched confirmation and the difference in readout signal is correlated to the expansion or degree of expansion or contraction relative to a the original configuration.

The embodiments discussed herein are illustrative of the present invention and reference to illustrations, modifications, or adaptations of the specific structures described herein will be readily apparent to those skilled in the art. All such modifications, adaptations, or variations that rely upon the teachings of the present invention, and through which these teachings have advanced the art, are considered to be within the spirit and scope of the present invention. Hence, these descriptions and drawings that are contained expressly herein should not be considered as unduly limiting the scope of the invention and the present invention is not to be construed as limited to only the specific examples described and illustrated herein.

We claim:

1. A sensor assembly comprising:
    an ionic material coated on a plurality of fibers, wherein the ionic material is circumferentially coated on an outer surface of the plurality of fibers;
    a conducting material contacting the ionic material at an interface between the conducting material and the plurality of fibers, wherein the conducting material is a layer engaging the circumferentially coated ionic material at the interface between the conducting material and the outer surface of the plurality of fibers;
    wherein the combination of the ionic material and the conducting material form a fabric-based pressure sensor yielding an electrical signal in response to pressure exerted on the sensor assembly.

2. The sensor assembly of claim 1, wherein the conducting material is discontinuous across the contact interface between the conducting material and the plurality of fibers.

3. The sensor assembly of claim 2, wherein the conducting material is patterned across the plurality of fibers.

4. The sensor assembly of claim 1 further comprising a nonconductive fabric layer.

5. The sensor assembly of claim 1, further comprising a heat bonding liner and wherein the conducting material is woven into a conductive fabric layer.

6. A sensor assembly comprising:
    an ionic material coated on a plurality of fibers,
    a conducting material contacting the ionic material at an interface between the conducting material and the plurality of fibers,
    a sealing material surrounding the ionic material and the conducting material;
    wherein the combination of the ionic material and the conducting material form a fabric-based pressure sensor yielding an electrical signal in response to pressure exerted on the sensor assembly.

7. A sensor assembly comprising:
    an ionic material formed as a plurality of nanofibers,
    a conducting material contacting the ionic material at an interface between the conducting material and the plurality of ionic nanofibers,
    wherein the combination of the plurality of ionic nanofibers and the conducting material form a fabric-based pressure sensor yielding an electrical signal in response to pressure exerted on the sensor assembly.

8. The sensor assembly of claim 7, wherein the conducting material is patterned across the plurality of ionic nanofibers.

9. The sensor assembly of claim 7 further comprising a nonconductive fabric layer.

10. The sensor assembly of claim 7, wherein the conducting material is woven into a conductive fabric layer.

11. The sensor assembly of claim 7, further comprising a heat bonding liner.

12. The sensor assembly of claim 7, further comprising a sealing material surrounding the plurality of ionic nanofibers and the conducting material.

\* \* \* \* \*